(12) United States Patent
Lavash et al.

(10) Patent No.: US 7,857,799 B2
(45) Date of Patent: Dec. 28, 2010

(54) ABSORBENT ARTICLE

(75) Inventors: Bruce William Lavash, Cincinnati, OH (US); Jean Jianqun Zhao, Cincinnati, OH (US); Denise Jean Bien, Cincinnati, OH (US); Ann-Marie Ventura, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 771 days.

(21) Appl. No.: 11/713,841

(22) Filed: Mar. 5, 2007

(65) Prior Publication Data

US 2008/0221541 A1    Sep. 11, 2008

(51) Int. Cl.
*A61F 13/15* (2006.01)
*A61F 13/20* (2006.01)

(52) U.S. Cl. .............. 604/385.17; 604/385.01; 604/385.101; 604/385.201; 604/385.31

(58) Field of Classification Search ............ 604/385.01, 604/385.17, 385.101, 385.201, 385.31
See application file for complete search history.

(56) References Cited

U.S. PATENT DOCUMENTS

| | | | |
|---|---|---|---|
| 4,846,824 A * | 7/1989 | Lassen et al. | 604/385.17 |
| 5,197,959 A | 3/1993 | Buell | |
| 6,394,989 B2 * | 5/2002 | Mizutani | 604/385.01 |
| 6,398,770 B1 | 6/2002 | Drevik | |
| 6,410,822 B1 | 6/2002 | Mizutani | |
| 6,413,248 B1 | 7/2002 | Mizutani | |
| 6,447,496 B1 | 9/2002 | Mizutani | |
| 6,471,682 B2 | 10/2002 | Kashiwagi | |
| 6,676,649 B2 | 1/2004 | Mizutani | |
| 2005/0004547 A1 | 1/2005 | Lavash | |
| 2005/0267433 A1 | 12/2005 | Tanio et al. | |
| 2005/0267434 A1 | 12/2005 | Tanio et al. | |
| 2005/0267435 A1 | 12/2005 | Tanio et al. | |

(Continued)

FOREIGN PATENT DOCUMENTS

WO    WO 02/47594 A1    6/2002

(Continued)

OTHER PUBLICATIONS

U.S. Appl. No. 11/713,960, filed Mar. 5, 2007, Jean J. Zhao et al.

(Continued)

*Primary Examiner*—Jacqueline F. Stephens
(74) *Attorney, Agent, or Firm*—Amanda T. Barry; Gary J. Foose

(57) ABSTRACT

A feminine hygiene device. The absorbent core can have a first compressibility in an unaltered state, wherein at least a portion of the absorbent core that is generally aligned with the longitudinal axis of the absorbent core has a second compressibility in an altered state. The second compressibility can be greater than the first compressibility. The portion of the absorbent core having the second compressibility can be a portion of the absorbent core from which absorbent material has not been completely removed. The feminine hygiene device has an elastic member generally aligned with the core longitudinal axis and spanning at least a portion of the absorbent core that has a preferentially weakened zone of compression. A portion of the absorbent core that is generally aligned with the core longitudinal axis can comprise structural features selected from the group consisting of slits, corrugations, nodules, and tufts.

20 Claims, 29 Drawing Sheets

U.S. PATENT DOCUMENTS

2006/0184150 A1  8/2006  Noel

FOREIGN PATENT DOCUMENTS

| WO | WO 02/085269 A1 | 10/2002 |
| WO | WO 02/085270 A1 | 10/2002 |
| WO | WO 02/087483 A1 | 11/2002 |
| WO | WO 02/087484 A1 | 11/2002 |
| WO | WO 03/047484 A1 | 6/2003 |
| WO | WO 03/059222 A1 | 7/2003 |

OTHER PUBLICATIONS

U.S. Appl. No. 11/714,020, filed Mar. 5, 2007, Jean J. Zhao et al.

U.S. Appl. No. 11/713,992, filed Mar. 5, 2007, Jean J. Zhao.

U.S. Appl. No. 11/714,021, filed Mar. 5, 2007, Jean J. Zhao.

Stayfree Dry Max Ultra Thin, Distributed by Personal Products Company, Division of McNeil-PPC Inc., Skillman, NJ 08558.

Office Action for U.S. Appl. No. 11/713,960 dated Nov. 20, 2009; Zhao et al.; filed Mar. 5, 2007.

Office Action for U.S. Appl. No. 11/713,960 dated Jun. 8, 2009; Zhao et al.; filed Mar. 5, 2007.

Office Action for U.S. Appl. No. 11/713,960 dated Jan. 6, 2009; Zhao et al.; filed Mar. 5, 2007.

Office Action for U.S. Appl. No. 11/713,960 dated Jun. 20, 2008; Zhao et al.; filed Mar. 5, 2007.

* cited by examiner

ABSORBENT ARTICLE

FIELD OF THE INVENTION

The present invention relates to improved fit for absorbent articles such as menstrual pads, pantiliners, and incontinence pads.

BACKGROUND OF THE INVENTION

Feminine hygiene devices such as sanitary napkins and pantiliners are designed to collect, absorb, and retain bodily discharges. Feminine hygiene devices typically comprise a liquid pervious topsheet, an absorbent core, and a liquid impervious backsheet. Feminine hygiene devices are typically attached to the wearer's panty with a pressure sensitive adhesive to keep the feminine hygiene device under the wearer's vaginal opening and near the wearer's body to intercept discharge.

Approaches for achieving proper fit include using shaped absorbent cores and shaped inserts to shape the feminine hygiene device. Feminine hygiene devices having these features may not be able to be folded flat. Packaging feminine hygiene devices that cannot be folded flat can be inconvenient and uneconomical. Furthermore, shaped elements may not be sufficiently pliable to conform to a wide range of motions and may feel bulky to wearers of the feminine hygiene device.

To perform optimally, feminine hygiene devices should conform to the shape of the woman's pudendal region. Presently, some designers believe that the coronal profile of a feminine hygiene device should have the shape of an inverted "V" in the rear to fit between the woman's buttocks and have a "W" shape in the middle to fit around her labia. Some designers also believe that a feminine hygiene device should be slightly cup-shaped in the woman's pubic area. Some designers believe that these shapes should not merely project from a flat feminine hygiene device but should be contours along a feminine hygiene device that is curved from front to rear to fit with the curvature of the wearer's pudendal region as viewed from a sagittal perspective. For feminine hygiene devices having a "W" shaped middle area and an inverted "V" shaped rear area, there can be a ridge along a portion of the length of the feminine hygiene device defined by the middle vertex of the "W" and the vertex of the inverted "V."

For the ridge to bend to conform to the curvature of the wearer's pudendal region as viewed from a sagittal perspective, the ridge must be shortened. Conventional materials and structures for absorbent cores may be unable to shorten, in a controlled manner, along the ridge as the absorbent core is bent. Rather, as the ridge is shortened by bending, the absorbent core material buckles, crumples, and wrinkles in an uncontrolled manner. An absorbent core that is buckled, crumpled, and wrinkled in an uncontrolled manner along the ridge is unlikely to conform to the wearer's body satisfactorily. For wetted absorbent cores, buckling, crumpling, and wrinkling can be even more pronounced due to the loss of mechanical integrity caused by wetting.

A simple physical model illustrative of the problem facing designers of feminine hygiene devices having a "W" shaped middle area, an inverted "V" shaped rear area, and a ridge along a portion of the length of the feminine hygiene device can be created using a rectangular sheet of writing paper. The writing paper is folded in half such that the fold line has the same length as and is aligned with the longer dimension of the writing paper. Next the fold is opened slightly. This creates a "beam" having an inverted "V" cross section. When the beam is bent along the length of the beam, such that the fold line is on the side of the beam being shortened by compressive stresses, the fold line buckles, crumples, and wrinkles uncontrollably.

One approach for allowing the ridge of the feminine hygiene device to be shortened without uncontrollably deforming the absorbent core is to remove absorbent material from the absorbent core in areas where shortening occurs. As the core is bent, the openings created by removing absorbent material can close, thereby allowing controlled shortening of and along the ridge. Openings in the absorbent core can adversely interrupt fluid transport in the absorbent core, can be challenging to manufacture, and can reduce the structural integrity of the absorbent core.

Accordingly, there is a need for feminine hygiene devices that can conform to the shape of a woman's pudendal region as she moves through her day. There is also a need for feminine hygiene devices that can conform to the shape of a woman's pudendal region and be folded flat for packaging and storage. A further need is for feminine hygiene devices having an absorbent core that performs effectively when portions of the absorbent core are shortened.

SUMMARY OF THE INVENTION

A feminine hygiene device comprising an absorbent core is disclosed. The absorbent core comprises absorbent material and has a core longitudinal axis. The absorbent core has a first compressibility in an unaltered state. At least a portion of the absorbent core has a second compressibility in an altered state. At least a portion of the absorbent core that is generally aligned with the core longitudinal axis has a second compressibility in an altered state. The second compressibility is greater than the first compressibility. The portion of the absorbent core having the second compressibility is a portion of the absorbent core from which absorbent material has not been completely removed. The feminine hygiene device comprises an elastic member. The elastic member spans at least a portion of the absorbent core having the second compressibility. The elastic member is operatively related to the absorbent core. The elastic member is generally aligned with the core longitudinal axis. A portion of the absorbent core that is generally aligned with the core longitudinal axis can comprise structural features selected from the group consisting of slits, corrugations, nodules, and tufts.

DETAILED DESCRIPTION OF THE INVENTION

The benefits of the present invention can be enjoyed in virtually all feminine hygiene devices designed to be worn in the panties of the wearer, such as sanitary napkins, pantiliners, and light incontinence products. For convenience and clarity, the invention is disclosed in an embodiment of a sanitary napkin.

As used herein the term "joined" refers to the condition in which a first member is attached, or connected, to a second member either directly; or indirectly, in which the first member is attached, or connected, to an intermediate member which in turn is attached, or connected, to the second member.

Figure 1:
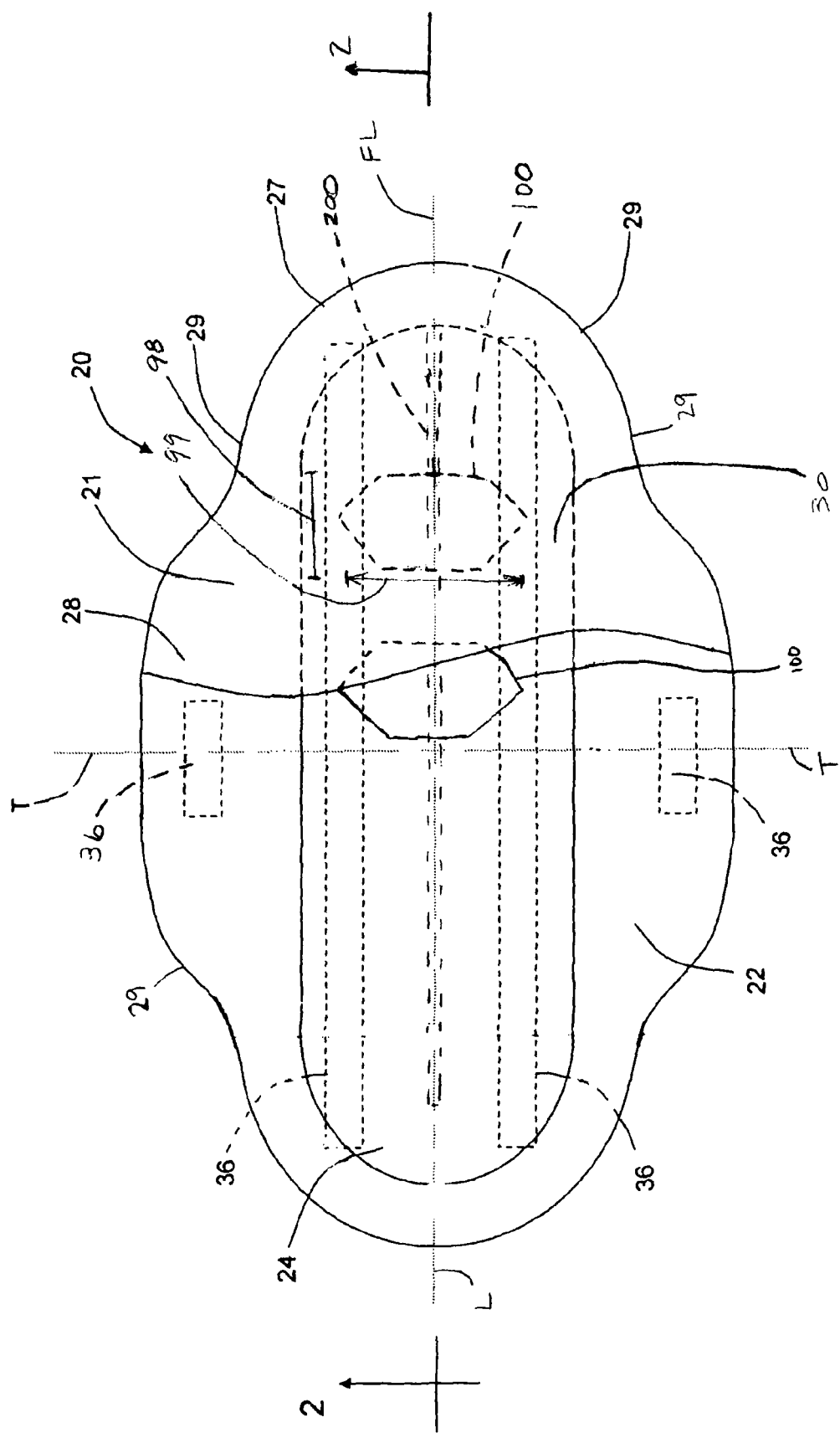
FIG. 1 is an embodiment of a feminine hygiene device.

FIG. 1 is a partial cut away plan view of one embodiment of a feminine hygiene device 20 providing for improved static and dynamic body fit. The feminine hygiene device 20 can be comprised of a topsheet 21, a backsheet 22 joined to the topsheet 21, and an absorbent core 24 disposed between the topsheet 21 and the backsheet 22. The feminine hygiene device 20 has a longitudinal axis FL. The absorbent core 24 has a core longitudinal axis L generally coinciding with the longitudinal axis FL of the feminine hygiene device 20. The absorbent core 24 can have a first compressibility in an unaltered state, wherein at least a portion of the absorbent core 24 that is generally aligned with the core longitudinal axis has a second compressibility in an altered state. The second compressibility can be greater than the first compressibility. The portion of the absorbent core 24 having the second compressibility can be a portion of the absorbent core 24 from which absorbent material has not been completely removed. That is, when the absorbent core 24 is in a relaxed state, there are no apertures, slots, or holes created by completely removing material. The portion of the absorbent core 24 having a second compressibility in an altered state can be a preferentially weakened zone of compression 100. The portion of the absorbent core 24 having a second compressibility in an altered state can encompass the entire absorbent core 24. A preferentially weakened zone of compression 100 can be formed in a core in which the entire core has been altered by providing stiffening features, such as adhesives, channels, or other features, to bound the preferentially weakened zone of compression 100 or by providing a stiffening treatment to the material surrounding the preferentially weakened zone of compression 100.

The topsheet 21 and backsheet 22 can be joined about a periphery 27. An optional secondary topsheet can be disposed between the absorbent core 24 and topsheet 21. Secondary topsheets are often referred to as a distribution layer, which can be an absorbent material having fluid handling properties suitable for rapidly distributing fluid in a lateral direction. An optional second absorbent core can be disposed between the absorbent core 24 and the backsheet 22 and can also have a first compressibility in an unaltered state wherein at least a portion of the second absorbent core that is generally aligned with the core longitudinal axis L has a second compressibility in an altered state wherein the second compressibility is greater than the first compressibility.

The feminine hygiene device 20 can further comprise an elastic member 200 spanning at least a portion of the absorbent core 24 having the second compressibility. The elastic member 200 can span at least a portion of the absorbent core 24 comprising a preferentially weakened zone of compression 100. The elastic member 200 can be generally aligned with the core longitudinal axis L.

Absorbent core 24 comprises absorbent material and can be formed from any of the materials known to those skilled in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Absorbent core 24 can be a fibrous material. Absorbent core 24 can be relatively thin, less than about 5 mm in thickness, or less than about 3 mm in thickness, or less than about 1 mm in thickness. Thickness can be determined by measuring the thickness at the midpoint along the longitudinal centerline of the absorbent core 24 by any means known in the art for doing so while under a uniform pressure of 1.7 kPa. Absorbent core 24 can comprise absorbent gelling materials (AGM), including AGM fibers.

Absorbent core 24 can be formed or cut to a shape, the outer edges of which define a core periphery. The shape of absorbent core 24 can be generally rectangular, circular, oval, elliptical, or the like. Absorbent core 24 can be generally centered with respect to the core longitudinal axis L and the transverse centerline of the absorbent core 24. The profile of absorbent core 24 can be such that more absorbent material is disposed near the center of the absorbent article. For example, the absorbent core can be thicker in the middle, and tapered at the edges in a variety of ways known in the art.

Feminine hygiene device 20, as well as each layer or component thereof can be described as having a "body facing" surface and a "garment facing" surface. The topsheet 21 has a body facing surface 30. Body facing surfaces are layers or components that are oriented closer to the body when in use, and the garment facing surfaces are the surfaces that are oriented closer to the undergarment of the user when in use.

Feminine hygiene device 20 has a transverse axis T. Longitudinal axis FL and transverse axis T define a two-dimensional plane of the feminine hygiene device 20 prior to use. The feminine hygiene device 20 has a length, which is the longest dimension measured generally parallel to the longitudinal axis FL. The feminine hygiene device 20 has a width. In general, the width can be measured between lateral edges 29 in a direction generally parallel to transverse axis T. The width can vary or be generally constant along the length of the feminine hygiene device 20.

Feminine hygiene device 20 can have side extensions 28, commonly referred to as "wings," designed to wrap around the sides of the pudendal region of the panties of the user of feminine hygiene device 20. Feminine hygiene device 20 and/or side extensions 28 can have fastening means, including attachment components, such as pressure sensitive adhesives, or mechanical fasteners such as hook and loop fasteners.

The fastening means can include attachment components such as panty fastening adhesive 36 disposed on the side extensions 28, as shown in FIG. 1.

The feminine hygiene device 20 can be made by hand or on commercial high-speed production lines.

To conform to the wearer's body, both statically and dynamically, the feminine hygiene device 20 should be able to bend about multiple axes. The feminine hygiene device 20 needs to be able to bend so that the feminine hygiene device 20 can deform to have the desired coronal profile (generally a "W" shape in the middle area and an inverted "V" in the rear area) and the desired sagittal profile (generally following the curve of the wearer's pudendal region from front to rear).

Absorbent core 24, or portions thereof, can be rendered to have a second compressibility in an altered state that is greater than a first compressibility in an unaltered state by altering the absorbent core 24. An absorbent core 24 can be more compressible in an altered state than an absorbent core 24 in an unaltered state because structure of the absorbent core 24 in a deformed state is molested.

Forces and stresses applied to the absorbent core 24 are carried and/or distributed to portions of the absorbent core 24 by the constituent materials of the absorbent core 24. The observed physical behavior, such as compressibility, of the absorbent core 24 or portions of the absorbent core 24 that are deformed can be altered by disrupting or mangling the constituent materials of the absorbent core 24. Examples of mangling the constituent materials include, but are not limited to, reorienting the fibers, creating discontinuities in the fiber structure, forming out of plane deformations of the absorbent core 24, and stretching fibers.

In one embodiment, the feminine hygiene device 20, disclosed herein, achieves improved static and dynamic body fit by providing at least one preferentially weakened zone of compression 100 in the absorbent core 24, as shown in FIG. 1. A preferentially weakened zone of compression 100 can be a region or portion of the absorbent core 24 that has been rendered more easily compressible than adjacent, non-rendered regions so as to permit multi-axis bending of the absorbent core 24 and controlled shortening of the absorbent core 24 along the core longitudinal axis L. The term preferentially is used to indicate that the rendered region or portion is selected by the designer to be in a desired location. By controlled shortening, it is meant that the absorbent core 24, when shaped to have a W shape in the middle region, an inverted V shape in the rear, and a curved sagittal profile, is deformed in a predetermined manner and does not randomly or uncontrollably buckle, fold, and/or bend. A preferentially weakened zone of compression 100 is an area set off as distinct from surrounding or adjoining areas. A preferentially weakened zone of compression 100 can be rendered to be more compressible in a direction generally aligned with the longitudinal axis FL of the feminine hygiene device 20.

The absorbent core 24 can comprise more than one preferentially weakened zone of compression 100. The absorbent core 24 can comprise between about 1 and about 30 preferentially weakened zones of compression 100. The absorbent core 24 can comprise between about 2 and about 10 preferentially weakened zones of compression 100. Absorbent cores 24 comprising two, three, four, five, six, or more preferentially weakened zones of compression 100 can be practical. A preferentially weakened zone of compression 100 can have a width 99, as measured generally orthogonal to the core longitudinal axis L, from about 10 mm up to the entire width of the absorbent core 24. A preferentially weakened zone of compression 100 can have a width 99 between about 25 mm and about 50 mm. A preferentially weakened zone of compression 100 can have a width 99 of about 39 mm. For absorbent cores comprising two or more preferentially weakened zones of compression 100, each preferentially weakened zone of compression 100 can have the same width 99 as other preferentially weakened zones of compression 100 or the widths 99 of the preferentially weakened zones of compression 100 can differ from one another.

In one embodiment, a preferentially weakened zone of compression 100 can extend along substantially the entire core longitudinal axis L. In another embodiment, the preferentially weakened zone of compression 100 extends along about 2 mm or more of the length of the absorbent core 24. The length of the absorbent core 24 is the longest dimension of the absorbent core 24 measured generally parallel to the core longitudinal axis L. Alternatively, each preferentially weakened zone of compression 100 can have length 98, as measured generally along the core longitudinal axis L, between about 10 mm and about 60 mm. Each preferentially weakened zone of compression 100 can have a length 98 of about 23 mm.

Each preferentially weakened zone of compression 100 can be spaced apart from adjacent preferentially weakened zones of compression by about 2 mm to about 100 mm. Each preferentially weakened zone of compression 100 can be spaced apart from adjacent preferentially weakened zones of compression by about 1 mm to about 5 mm. The preferentially weakened zones of compression 100 can be spaced apart from one another along the core longitudinal axis L by about 2 mm to about 30 mm. The preferentially weakened zones of compression 100 can be spaced apart from one another along the core longitudinal axis L by about 9 mm.

The forces applied to the feminine hygiene device 20 disclosed herein can be relatively low, such as the forces applied by the wearer's labia while walking. Thus, while it is recognized that all materials typically used in a feminine hygiene device 20 have some compressibility, the portion(s) having the second compressibility are more compressible than the portion(s) having the first compressibility.

Figure 2:
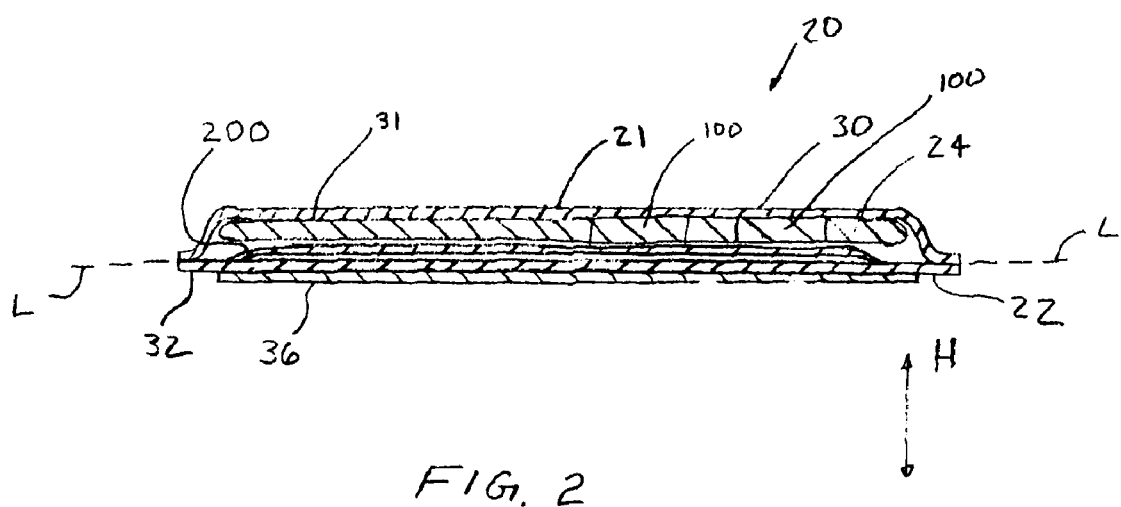
FIG. 2 is a cross section of FIG. 1 as indicated by section 2-2.

As shown in FIG. 2, the topsheet 21 has a topsheet body facing surface 30 (that can actually be a body contacting surface) and a topsheet garment facing surface 31 that can be adhered to the underlying absorbent core 24. The backsheet garment facing surface 32 is oriented closest to, and may contact, the wearer's panties in use (via adhesive attachment means, if used). The feminine hygiene device 20 can have strips of panty fastening adhesive 36 on the backsheet garment facing surface 32. The positioning adhesive can be hot-melt adhesive material capable of establishing a temporary bond with the undergarment material. Suitable materials include Findlay H2128 UN and Savare PM 17. Feminine hygiene device 20 has a vertical axis H.

Figure 3:
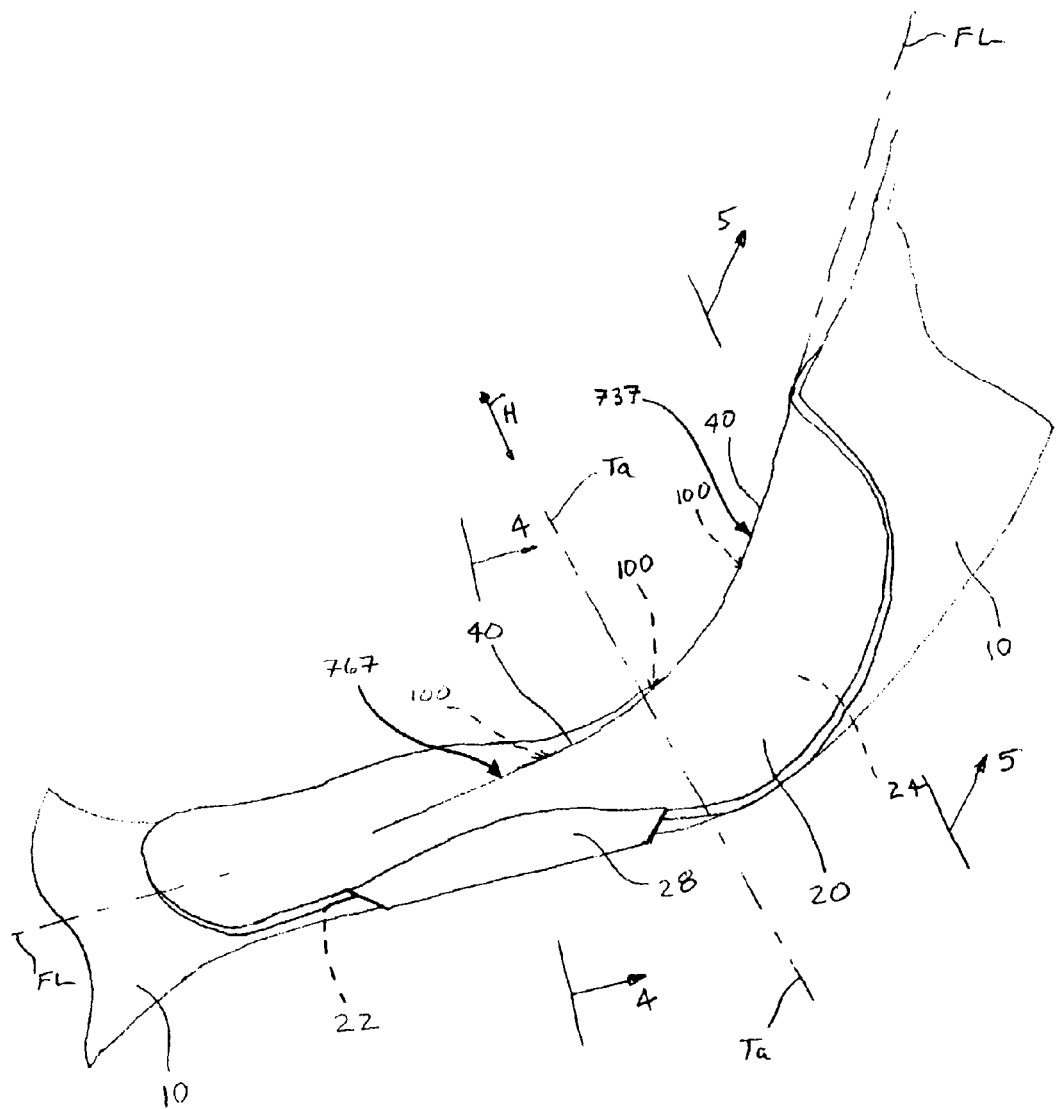
FIG. 3 is an embodiment of the feminine hygiene device in a panty.

A feminine hygiene device 20 having a shape that conforms to contours of a woman's pudendal region is shown in FIG. 3. As shown in FIG. 3, the feminine hygiene device 20 is bent about the longitudinal axis FL to form an inverted "V" shape, which can be bent about an axis parallel to transverse axis T and/or about an axis parallel to vertical axis H. This multi-axis bending provides for better body fit and comfort, since the absorbent core 24 and topsheet 21 can conform to the woman's body in three-dimensions about multiple axes, and move with the wearer's body during movements such as walking or sitting.

FIG. 3 shows a simplified representation of a feminine hygiene device 20 of the present invention as it might look when worn in the panties 10 of a wearer. The backsheet 22 is fastened in a temporarily fixed relationship to the panties 10. Side extensions 28 can be wrapped about the elasticated side edges of the pudendal portion of the panties. In use, the feminine hygiene device 20 fits the curvature of the wearer's body by bending both about the longitudinal axis FL, about axes parallel to transverse axis T (such as representative parallel axis Ta shown in FIG. 3), and about axes parallel to the vertical axis H. Typical feminine hygiene devices are either flat with little or no ridge 40 and/or uncontrollably buckle and fold when deformed into the shape shown in FIG. 3. Uncontrolled bucking, folding, twisting, bunching, and/or crumpling, commonly referred to as "roping", caused by the forces of the wearer's body and panties are undesirable because these behaviors can result in poor conformity between the feminine hygiene device 20 and the wearer's body. As shown in FIG. 3, the feminine hygiene device 20 of the present invention can bend and articulate about multiple axes due to the presence of portion(s) of the absorbent core 24 having a second compressibility greater than the first compressibility.

As shown in FIG. 3, the entire feminine hygiene device 20 takes the preferred shape. This results in a better fitting device and also can provide for a panty that conforms to the wearer's crotch, crease of the perineum, and crease between her buttocks. Given the tight fitting outer garments that are popular in modern fashion, close conformation of the feminine hygiene device 20 can make the device more discrete to wear. Devices in which the backsheet and/or the majority (by mass or volume) of the absorbent core do not adopt the preferred shape may be uncomfortable and less discrete to wear.

Figure 4:
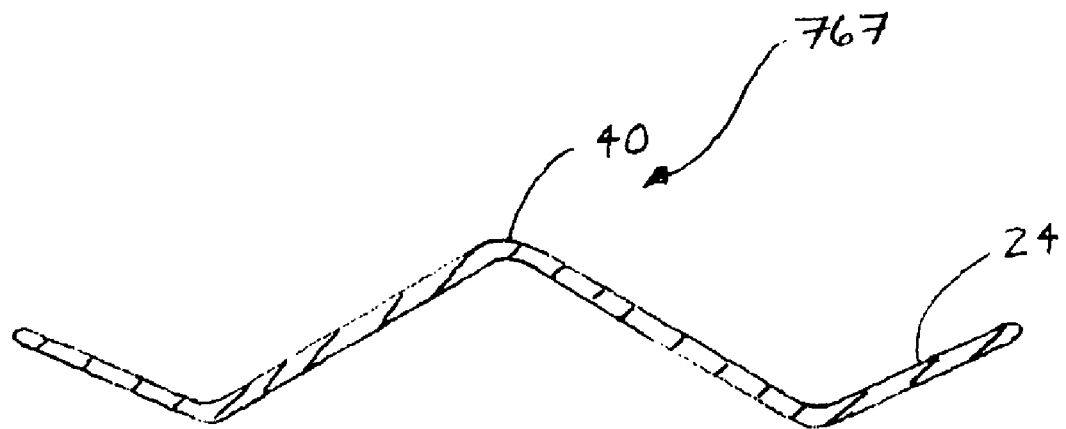
FIG. 4 is a cross section of FIG. 3 as indicated by section 4-4.
Figure 5:
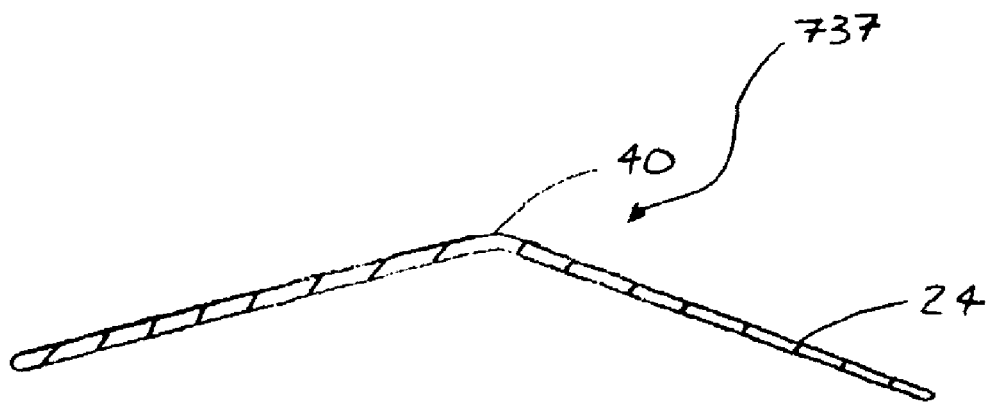
FIG. 5 is a cross section of FIG. 3 as indicated by section 5-5.

As shown in FIG. 3, and in the simplified schematic representations of FIGS. 4 and 5, a feminine hygiene device 20 of the present invention, when worn, is adapted to form a flattened or concave portion for positioning exterior of the clitoris and pubic area and a rearward portion adapted to yield a raised ridge 40 having a length and forming at least a portion of the pad into an inverted V shape for positioning in alignment with the creases of the perineum and buttocks. Such a configuration can be described in cross-section as an inverted V-shape, or as a "W" shape as shown in FIG. 4. The middle area 767 can have a W shape and the rear end area 737 can have an inverted V-shape.

Improved body fit and comfort of the feminine hygiene device 20 of the present invention is realized by the ability of the ridge 40 to articulate in a generally smooth, un-crumpled manner about axes parallel to either or both of the transverse axis T, longitudinal axis FL, and/or vertical axis H. Of course, the folds and bends of feminine hygiene device 20 can articulate about other axes, but, for simplicity of description, the articulation is described herein as being about the major axes of a three-dimensional orthogonal space.

A portion of the absorbent core having the second compressibility and/or a preferentially weakened zone of compression can be a compressible zone that shortens controllably, rather than kinks uncontrollably or takes a serpentine shape, when the ridge line 40 of an absorbent core having a ridge line 40 is bent about a curve. That is, the ridge line 40 can remain true to the core longitudinal axis L.

Figure 6:
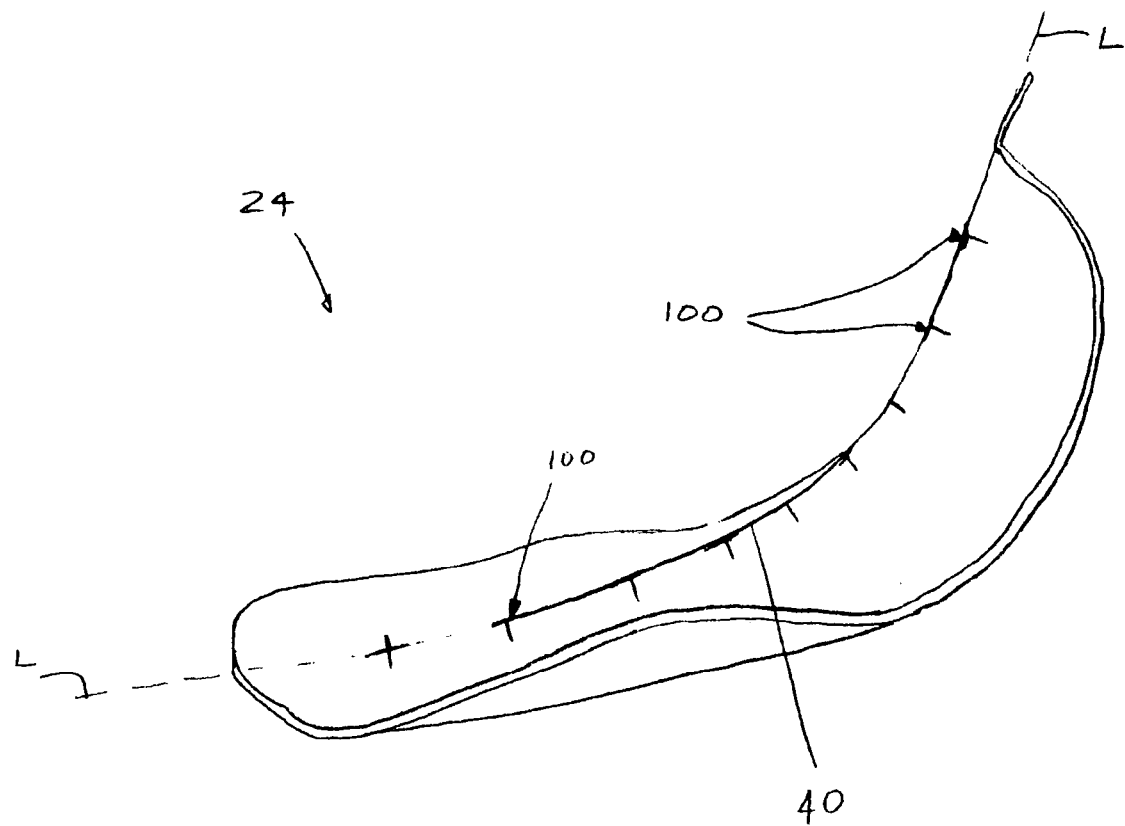
FIG. 6 is an embodiment of an absorbent core comprising slits.

FIG. 6 illustrates an absorbent core 24 deformed into a shape corresponding to the shape of the feminine hygiene device shown in FIG. 3. To arrange a generally flat absorbent core 24 into a shape corresponding to the shape of the feminine hygiene device 20 shown in FIG. 3, the absorbent core 24 can be shortened along the core longitudinal axis L as the ridge 40 aligns with a curved path to give the absorbent core 24 a three-dimensional shape.

One mechanism by which the absorbent core 24 can be shortened along the longitudinal axis is by compressing the material forming the absorbent core 24 along the core longitudinal axis L. The absorbent core 24 can be thought of as behaving like a structural beam having an inverted "V" cross-section. As the beam is bent upwards about a transverse axis, the core longitudinal axis L along the apex of the inverted "V" can shorten and/or the ends of the legs of the inverted "V" can extend in a longitudinal direction. No deformation occurs along the neutral axis of the inverted "V." The ridge 40 can be thought of as the apex of the inverted "V" and the legs of the inverted "V" are the edges of the absorbent core 24.

For absorbent cores typically used in feminine hygiene devices, such as air laid materials, the cores, when shaped as described herein and loaded in compression along the core longitudinal axis L, tend to fail in a buckling mode before they fail in compression. A ridge 40 that is buckled, wrinkled, or wadded may not conform to the shape of a woman's body as well as desired. Furthermore, for some non-woven materials, the resistance to buckling decreases with wetting. An absorbent core 24 having a portion or portions having a second compressibility in an altered state greater than a first compressibility in an unaltered state can permit shortening of the core longitudinal axis L in a controlled manner.

Figure 7:
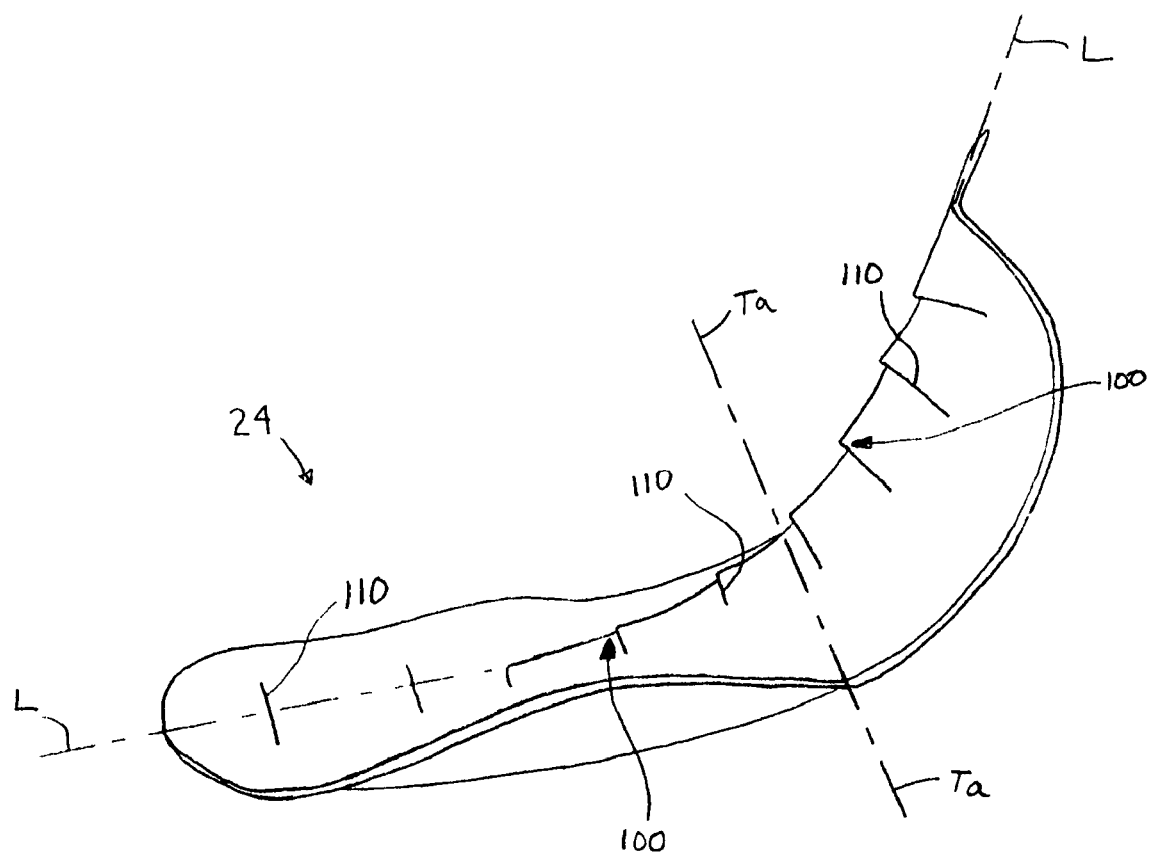
FIG. 7 is an embodiment of an absorbent core comprising slits.

The portion of the absorbent core 24 having a second compressibility can comprise structure allowing for portions of the absorbent core 24 along the core longitudinal axis L to slide over one another. Similar structures can be found in the scales of fish that allow the fish to bend. FIG. 7 illustrates an absorbent core 24 in which a portion of the absorbent core 24 having a second compressibility in an altered state has slits 110. The slits 110 can intersect the core longitudinal axis L. The slits 110 can be generally perpendicular to and intersect the core longitudinal axis L. The slits 110 can allow portions of the absorbent core 24 generally along the core longitudinal axis L to slide over or under one another. As the absorbent core 24 is bent about a parallel axis Ta, the slits 110 can allow portions of the absorbent core 24 adjacent to the slits 110 to articulate slightly out of plane relative to portions of the core without slits 110. Portions of the absorbent core 24 on opposing sides of a slit 110 can slide over or under one another. The compressibility of the portion of the absorbent core 24 having a second compressibility in an altered state can be controlled during manufacturing by altering the length of the slits 110 and by altering the spacing between slits along the core longitudinal axis L. Slits 110 can be distributed over the entire absorbent core 24, with slits 110 spaced apart from one another. The portion of the absorbent core 24 having a second compressibility in an altered state can comprise a single slit 110, can comprise a single slit 110 spaced apart from adjacent slits 110, and/or can comprise a plurality of slits 110 grouped near one another.

A preferentially weakened zone of compression 100 can comprise a single slit 110, a single slit 110 spaced apart from adjacent slits 110, and/or a plurality of slits 110 grouped near one another. A slit 110 can be a straight cut or a curved cut or combinations of curved and straight cuts.

Figure 8:
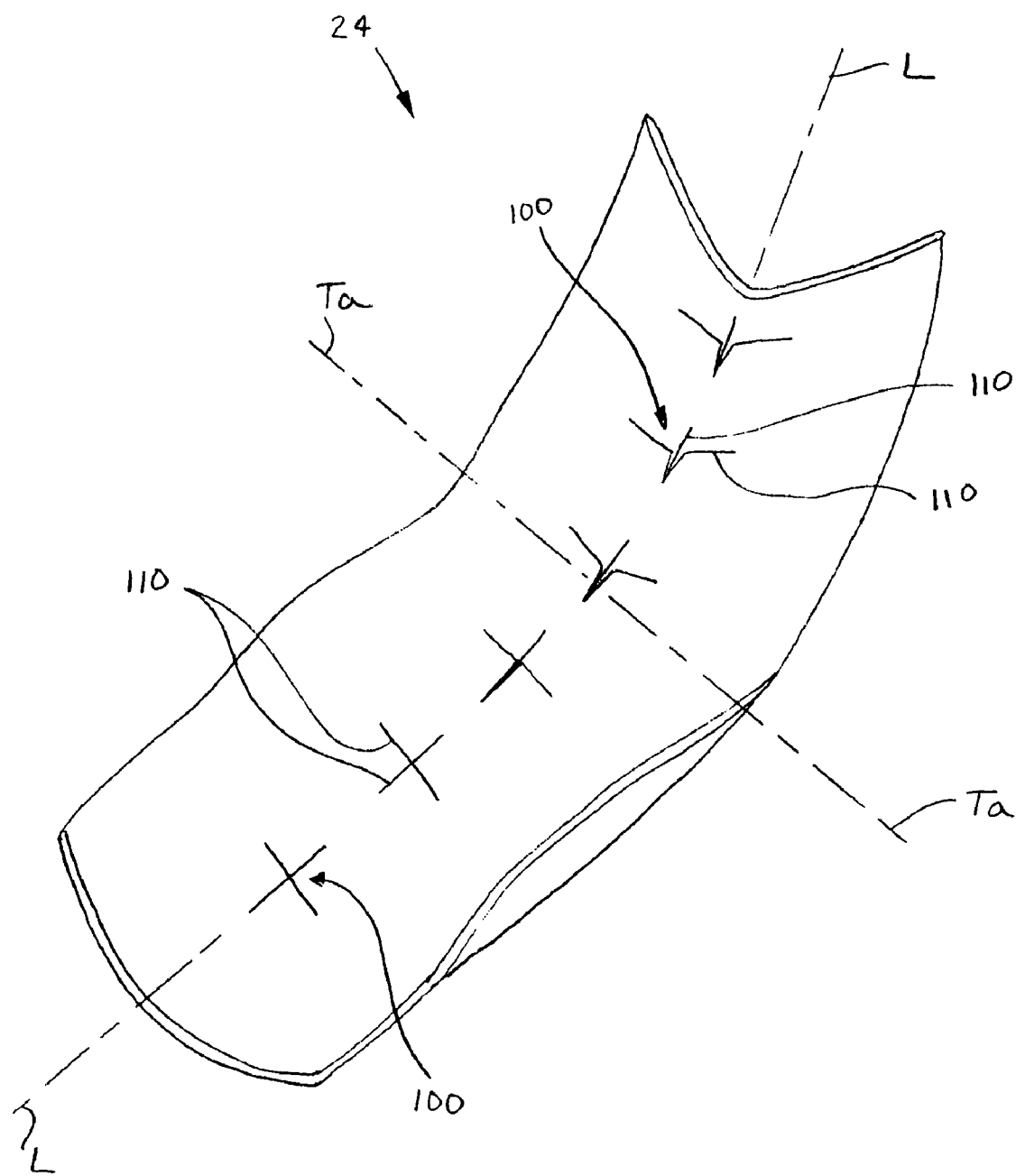
FIG. 8 is an embodiment of an absorbent core comprising intersecting slits.

FIG. 8 illustrates an absorbent core having intersecting slits 110 that are placed generally along the core longitudinal axis L, the intersecting slits 110 can be generally orthogonal to one another, and one of the intersecting slits 110 can be generally orthogonal to the core longitudinal axis L. The slits 110 aligned along the core longitudinal axis L allow the absorbent core 24 to be more easily formed into the "W" shape in the middle of the absorbent core 24 and the inverted "V" shape in the rear of the absorbent core 24.

Portions of the absorbent core 24 adjacent to each slit 110 orthogonal to the longitudinal axis can be thought of as being on the side of the slit oriented towards the rear of the absorbent core 24 or on the side of the slit oriented towards the front of the absorbent core 24. The location of the front and rear of the absorbent core can be understood by considering the ultimate use of the feminine hygiene device 20, the front of which is generally oriented towards the wearer's pubic area and the rear is generally oriented towards the wearer's anus. The portion of the absorbent core 24 on the side of the slit oriented towards the rear of the absorbent core 24 can slip over or under the portion of the absorbent core on the side of the slit oriented towards the front of the absorbent core, thereby allowing the core longitudinal axis L to shorten.

Figure 9:
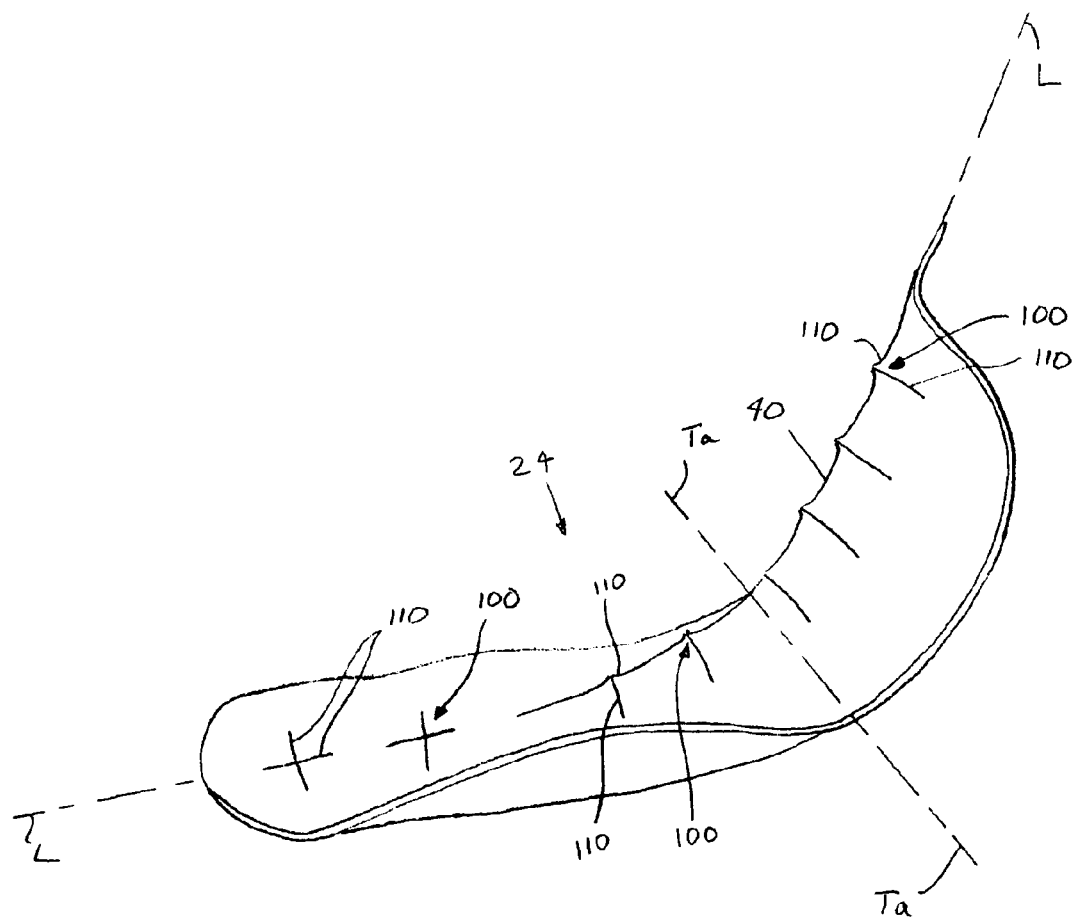
FIG. 9 is an embodiment of an absorbent core comprising intersecting slits.

Alternatively, the portions of the absorbent core 24 on opposite sides of a slit 110 intersecting the core longitudinal axis L may butt up against one another and be forced slightly out of plane with the ridge 40, as shown in FIG. 9. Without being bound by theory, it is believed that the slits 110 weaken portions of the absorbent core 24 proximal to the slits 110 and allow portions of the absorbent core 24 proximal to the slits 110 to easily be pushed slightly out of plane with the ridge 40 by the forces applied to the absorbent core 24 by the wearer's body.

Figure 10:
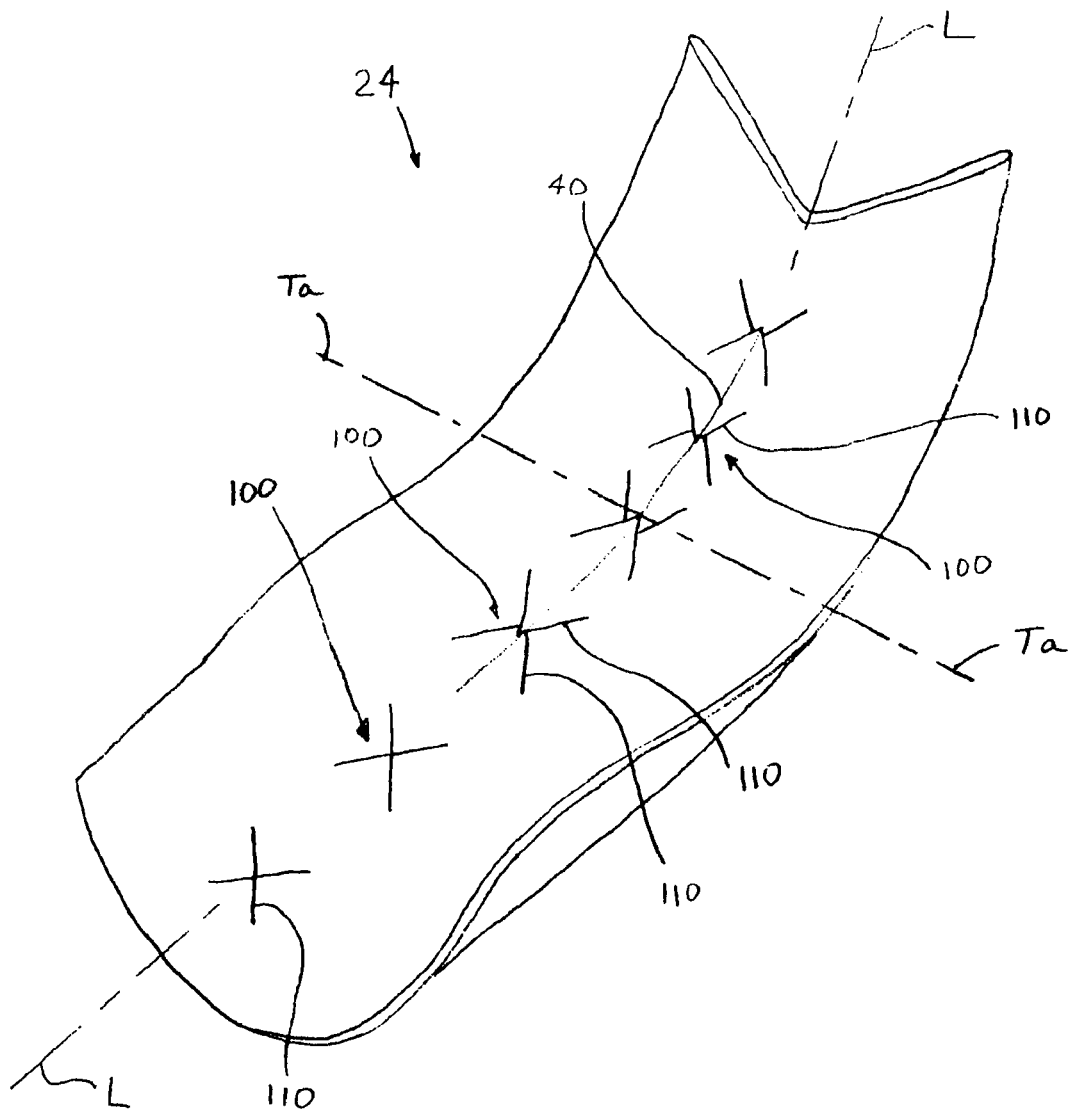
FIG. 10 is an embodiment of an absorbent core comprising intersecting slits.

FIG. 10 illustrates an absorbent core 24 having a second compressibility in an altered state comprising intersecting slits 110 generally along the core longitudinal axis L. The slit pattern shown in FIG. 10 can allow portions of the absorbent core 24 to be pushed slightly out of plane with the ridge 40. The ridge 40 is formed by portions of the absorbent core 24 between the vertices of the intersection of the slits 110 along the core longitudinal axis L. Portions of the absorbent core 24 adjacent to an individual slit 110 can either ride over or be pushed under the portions of the absorbent core on the other side of the slit 110, thereby allowing shortening of the core longitudinal axis L of the absorbent core 24. The slits 110 can intersect one another such a portion of one slit 110 lies on both sides of another slit 110. That is, the slits 110 cross one another.

Figure 11:
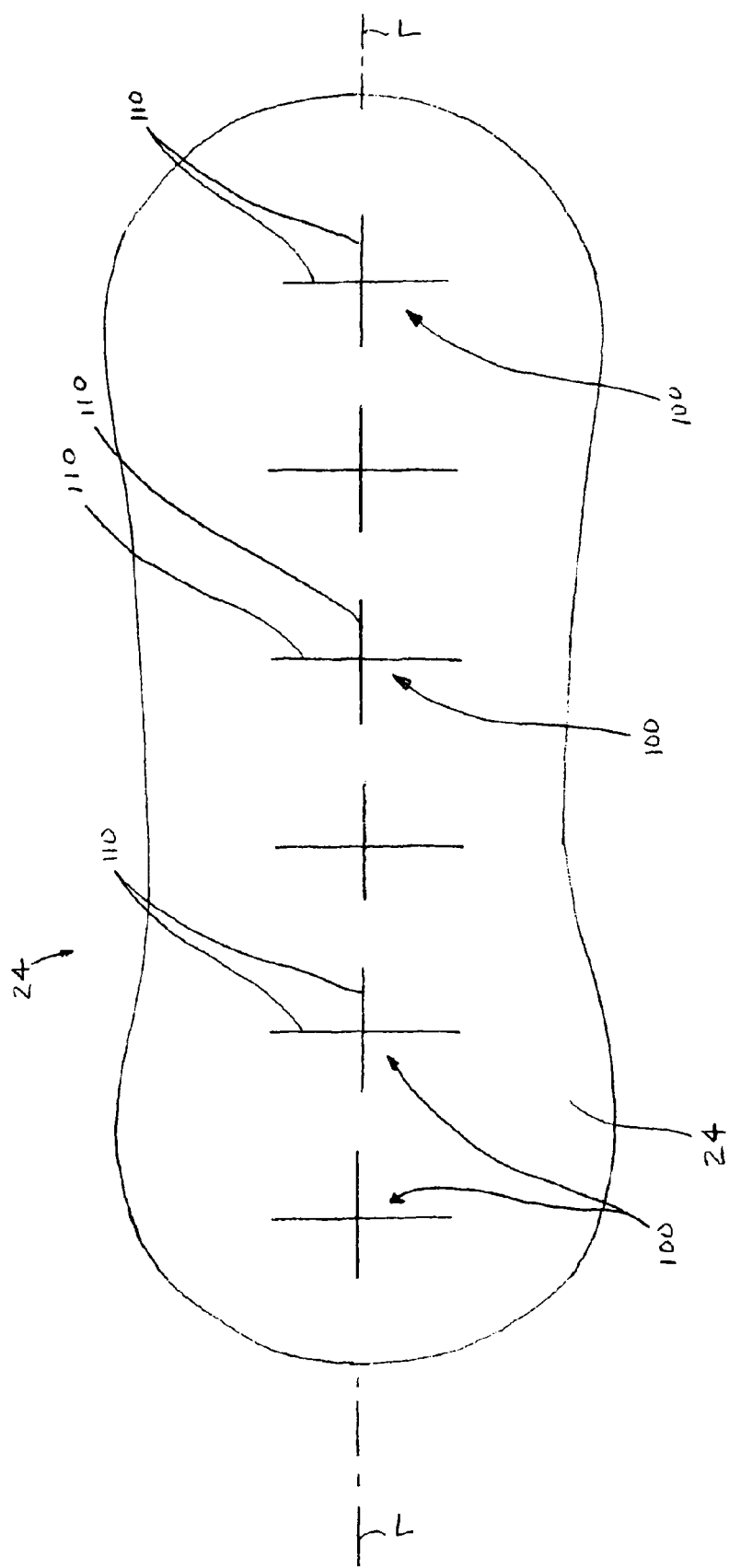
FIG. 11 is a slit pattern for an embodiment of the absorbent core.

In a manufacturing line, slits 110 can be formed by a roller having cutting blades. A pattern for slits 110 is shown in FIG. 11. The slits 110 intersecting the core longitudinal axis L can have a length between about 10 mm and about 60 mm. The slits 110 intersecting the core longitudinal axis L can have a length between about 25 mm and about 40 mm. The slits 110 intersecting the core longitudinal axis L can have a length of about 31 mm. The slits 110 aligned along the core longitudinal axis L can have a length between about 5 and about 60 mm. The slits 110 aligned along the core longitudinal axis L can have a length between about 15 mm and about 30 mm. The slits 110 aligned along the core longitudinal axis L can have a length of about 21 mm.

The slits 110 intersecting the core longitudinal axis L can be approximately bisected by the core longitudinal axis L or the slits 110 intersecting the core longitudinal axis L can be asymmetric to the core longitudinal axis L. For absorbent cores 24 comprising intersecting slits 110, the slits 110 intersecting the core longitudinal axis L and the slits 110 aligned along the core longitudinal axis L can bisect one another. Slits 110 can be oblique to the core longitudinal axis L.

The entire absorbent core 24 can comprise slits 110 such that the portion of the absorbent core 24 having a second compressibility in an altered state can encompass the entire absorbent core 24.

Figure 12:
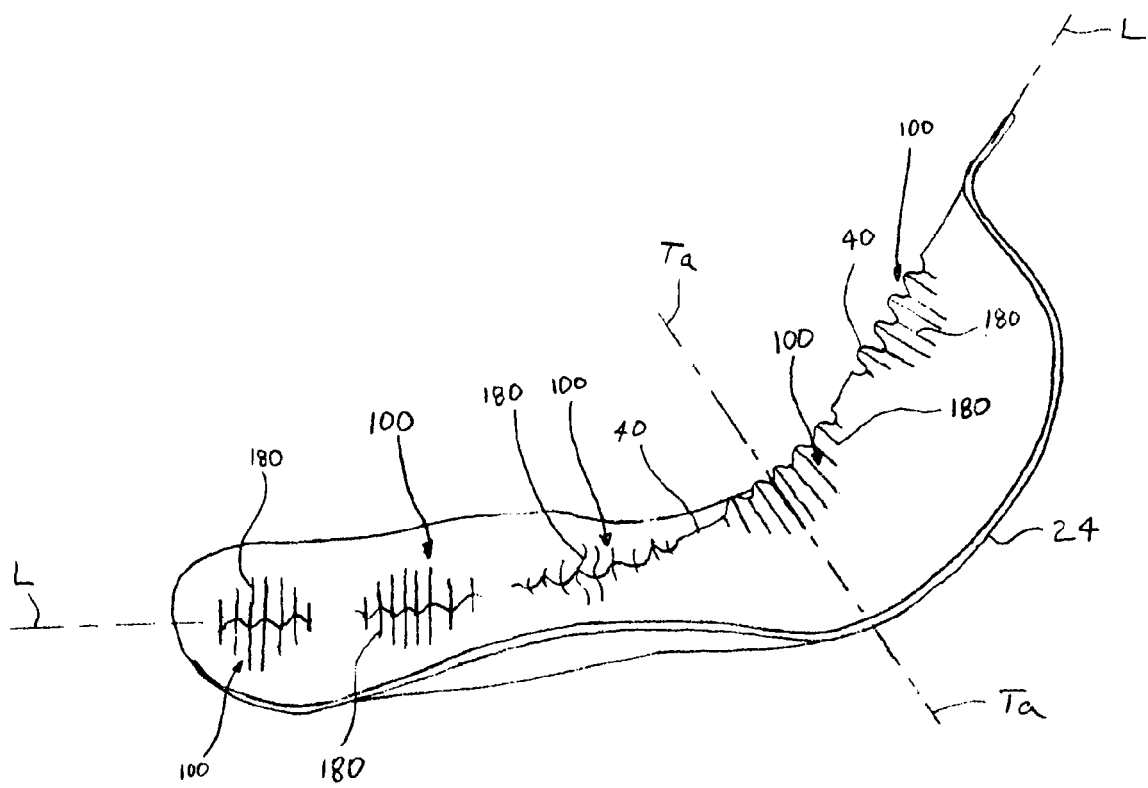
FIG. 12 is an embodiment of an absorbent core comprising corrugations.
Figure 13:
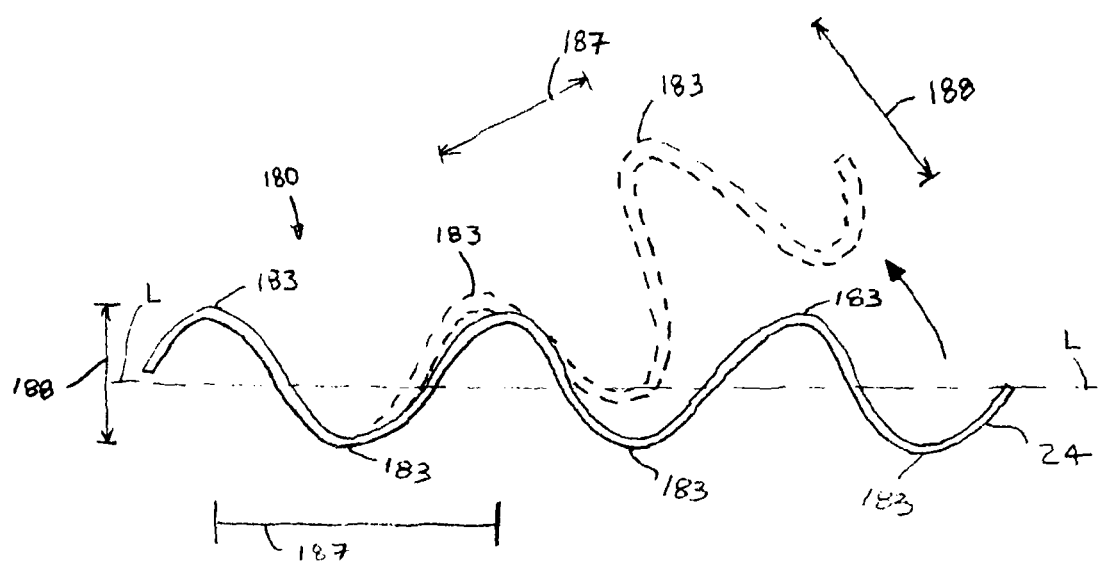
FIG. 13 is a schematic of the mechanical behavior a corrugated absorbent core.

FIG. 12 illustrates an absorbent core 24 in which a portion of the absorbent core having a second compressibility comprises corrugations 180. In FIG. 12, the portions of the absorbent core 24 having a second compressibility are illustrated as a preferentially weakened zone of compression 100. Corrugations 180 are portions of the absorbent core 24 that are deformed out of plane. The absorbent core 24 having corrugations 180 can be shortened along the core longitudinal axis L as the absorbent core 24 is bent about parallel axis Ta. The individual corrugations 180 are comprised of bumps 183, as shown in FIG. 13. Corrugations 180 extend across the core longitudinal axis L. Corrugations 180 can be approximately orthogonal to the core longitudinal axis L. Corrugations 180 can extend across the entire absorbent core 24. Individual corrugations 180 can extend across a portion of the absorbent core 24. The geometry of the corrugations 180 can vary along core longitudinal axis L. The shape of the corrugations 180 in the plan of the absorbent core 24 can be curved or straight or combinations of curved and straight portions. Corrugations 180 can have a length greater than about 10 mm, the length of a corrugation 180 being the extent of the corrugation 180 in a direction measured orthogonal to the core longitudinal axis L.

The preferentially weakened zone of compression 100 can be bound to discrete regions, as illustrated in FIGS. 1 and 12. The preferentially weakened zone of compression 100 can extend along the core longitudinal axis L. The entire absorbent core 24 can comprise corrugations such that the portion of the absorbent core 24 having a second compressibility in an altered state can encompass the entire absorbent core 24.

The compressibility of the portion or portions of the absorbent core 24 having a second compressibility can be controlled by altering one or more of the bump spacing 187, the bump height 188, and the length of the corrugations 180. If the bumps 183 are evenly spaced, the bump spacing 187 can be thought of as the wavelength of the corrugations 180, the corrugations 180 being viewed as a wave form. The bump spacing 187 can vary along the longitudinal axis L of the absorbent core 24. The bump height 188 can be thought of as the amplitude of the corrugations. The bump height 188 can vary along the longitudinal axis L of the absorbent core.

Bumps 183 can move more closely to one another, thereby allowing the ridge 40 to shorten. As the bumps 183 move more closely to one another, the bump height 188 can increase and the bump spacing 187 can decrease.

The bump spacing 187 in the uncompressed condition can be between about 0.5 mm and about 15 mm, and any dimensions there between in 0.5 mm increments from these values. The bump spacing 187 in the uncompressed condition can be between about 1 mm and about 7 mm. The bump spacing 187 in the uncompressed condition can be about 3 mm. The bump height 188 in the uncompressed condition can be between about 0.2 mm and about 10 mm, and any dimensions there between in 0.2 mm increments from these values. The bump height 188 in the uncompressed condition can be between about 0.5 mm and about 3 mm. The bump height 188 in the uncompressed condition can be about 1.5 mm.

Figure 14:
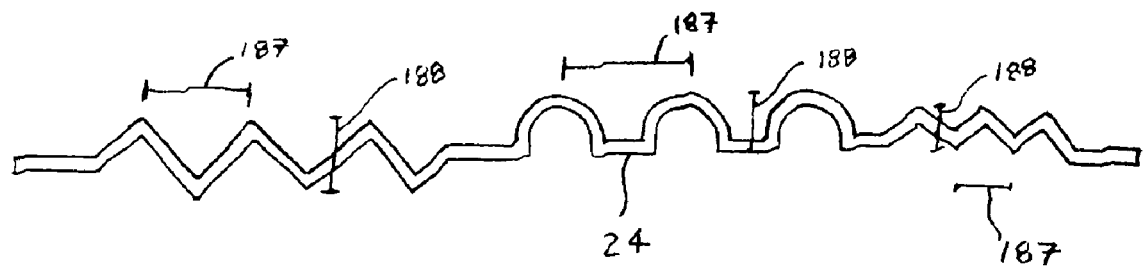
FIG. 14 is a schematic of examples of different shapes for corrugations

Corrugations 180 can be formed in the absorbent core 24 by hand or by feeding the absorbent core 24 through a pair of intermeshing toothed rollers in which the teeth are aligned perpendicular to the circumference of the roller. Corrugations 180 can be formed in the absorbent core 24 by the process known in the art as ring rolling, as disclosed in patents including U.S. Pat. Nos. 5,518,801, 5,914,084, 5,156,793, and 5,167,897. As the word corrugations is used herein, corrugations 180 can be structures produced by ring rolling. Persons skilled in the art recognize that ring rolling in which the teeth and grooves are oriented circumferentially about the rotating rollers tends to produce an incrementally stretched web, portions of which are deformed out of plane. Corrugations 180 produced by ring rolling can behave similarly to corrugations 180 formed by rollers in which the teeth are aligned perpendicular to the circumference of the roller, with respect to the corrugated absorbent core 24 being capable of controlled compression along the core longitudinal axis L. The absorbent core 24 can be fed through the ring rolling apparatus such that the core longitudinal axis L is generally aligned with the direction of travel through the ring rolling apparatus with the grooves of the ring rolling apparatus arranged on the rollers axially. The absorbent core 24 can be fed through the ring rolling apparatus such that the core longitudinal axis L is generally orthogonal with the direction of travel of the ring rolling apparatus with the groves of the ring rolling apparatus arranged on the rollers circumferentially. Corrugations 180 can have a variety of shapes in profile, non-limiting examples of which are shown in FIG. 14.

Figure 15:
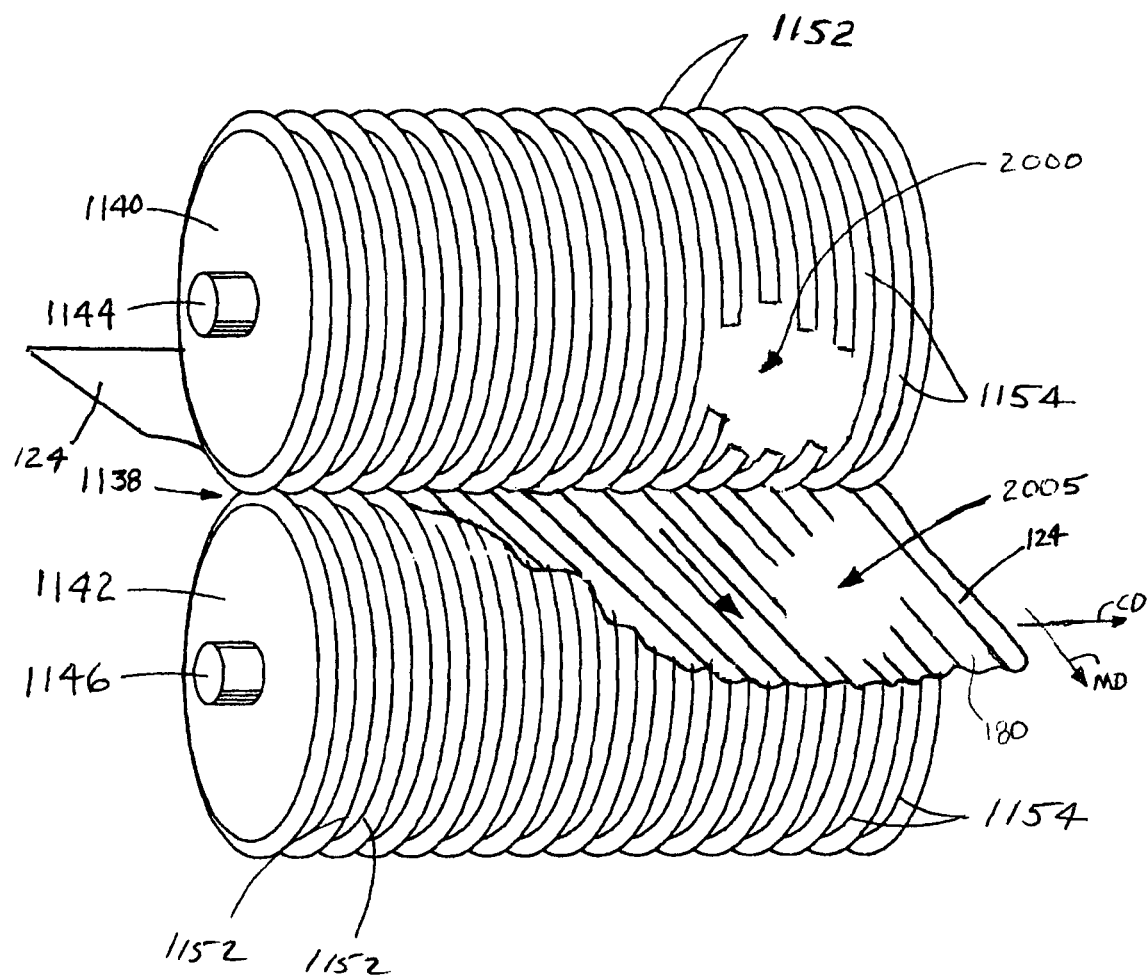
FIG. 15 is a schematic of an apparatus for forming corrugations in an absorbent core.

As shown in FIG. 15, absorbent core web 124 can be fed through the ring rolling apparatus, traveling in the direction indicated by the arrow. The machine direction MD and the cross direction CD are indicated in FIG. 15. For an absorbent core web 124 fed through the ring rolling apparatus shown in FIG. 15, the core longitudinal axis L of the absorbent core 24 formed from the absorbent core web 124 can be generally orthogonal with the direction of travel so that the corrugations 180 can extend across the core longitudinal axis L, as shown in FIG. 12. Absorbent core web 124 can be fed to the nip 1138 formed by a pair of opposed forming rolls 1140 and 1142. Forming rolls 1140 and 1142 are carried on respective rotatable shafts 1144, 1146, having parallel axes of rotation. Forming rolls 1140 and 1142 can include a plurality of axially-spaced, side-by-side, circumferentially-extending, equally-configured raised portions 1152 that can be in the form of thin fins of substantially rectangular cross section, or they can have a triangular or an inverted V-shape when viewed in cross section. If they are triangular, the vertices of raised portions 1152 are outermost with respect to the surface of forming rolls 1140 and 1142. The outermost tips of the raised portions 1152 can be rounded to avoid cuts or tears in the absorbent core web 124 as the absorbent core web 124 passes between the rolls.

The spaces between adjacent raised portions 1152 can define recessed, circumferentially-extending, equally configured grooves 1154. The grooves 1154 can have a substantially rectangular cross section when the raised portions 1152 have a substantially rectangular cross section, and they can be of inverted triangular cross section when the raised portions 1152 have a triangular cross section. Thus, each of forming rolls 1140 and 1142 can include a plurality of spaced raised portions 1152 and alternating grooves 1154 between each pair of adjacent raised portions 1152. The raised portions 1152 and the grooves 1154 need not each be of the same width, however, and the grooves 1154 can have a larger width than that of the raised portions 1152, to permit the material that passes between the interengaged rolls to be received within the respective grooves 1154 and to be locally stretched.

Portions of forming rolls 1140 and 1142 can be without raised portions 1152 and grooves 1154, as shown in FIG. 15, so that undeformed portions 2005 of the absorbent core web 124 can be formed. Forming roll 1142 can also have an untooled region that is circumferentially coordinated with an untooled region 2000 of forming roll 1140.

Figure 16:
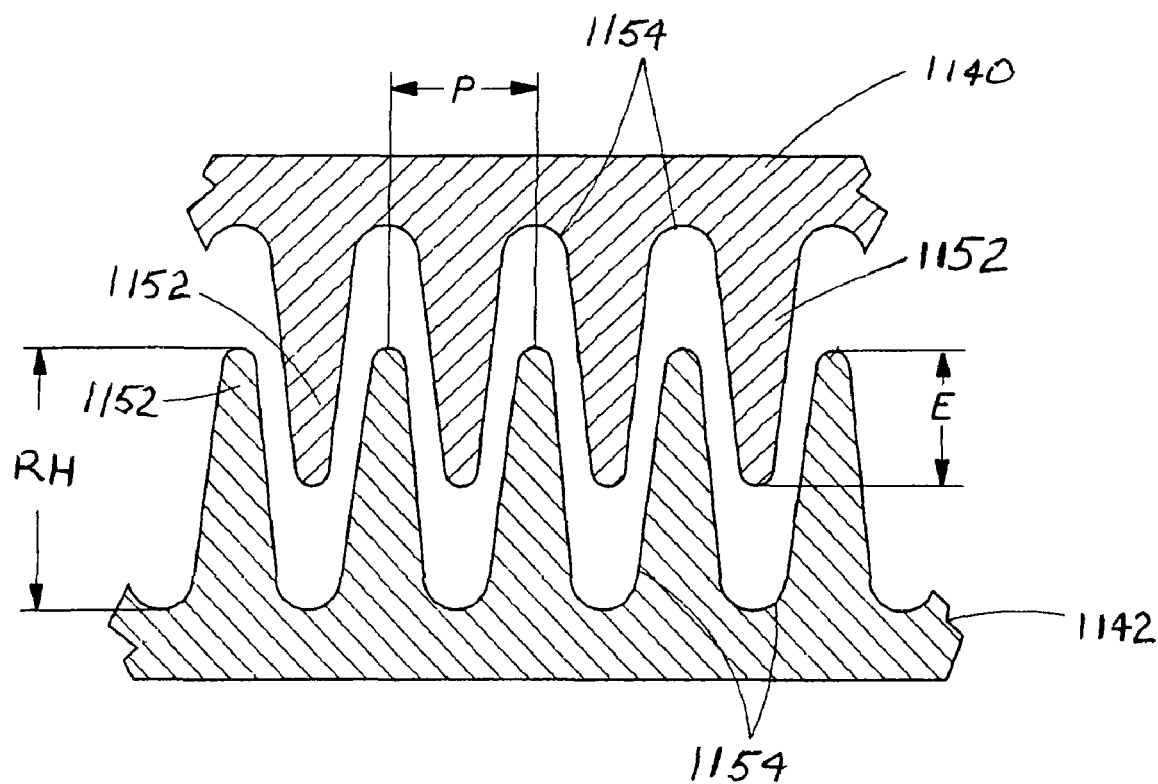
FIG. 16 is a schematic of interengaged forming rolls.

A cross-sectional view showing the interengagement of raised portions 1152 and grooves 1154 of the respective rolls is shown in FIG. 16. Raised portions 1152 have a raised portion height RH and can be spaced apart from one another by a uniform distance to define a pitch P (note that RH can also be applied to groove depth; in one embodiment raised portion height RH and groove depth can be equal). As shown, raised portions 1152 of one roll can extend partially into grooves 1154 of the opposed roll to define a "depth of engagement," E. The respective axes of rotation of forming rolls 1140 and 1142 are spaced from each other such that there is a predetermined space or gap between the opposed sidewalls of the interengaged raised portions 1152 and grooves 1154 of the respective rolls.

Each raised portion 1152 can be of the same size so that each of the opposed raised portions 1152 and grooves 1154 on respective forming rolls 1140 and 1142 can interengage with each other along the entire axial lengths of each of the rolls. The depth of engagement E, raised portion height RH, and pitch P can be varied as desired depending on the properties of the absorbent core web 124 being processed and the desired characteristics of the absorbent core 24.

By way of example and not to be limiting, raised portions 1152 having a peak-to-peak pitch P of the order of about 3.81 mm, having sidewalls disposed at an included angle of the order of about 12°, having a uniformly rounded ridge tip radius, and having a tip-to-base raised portion height RH (and groove depth) of the order of about 0.762 mm can be used. The sizes of the respective ridges and grooves can be varied within a wide range.

Figure 17:
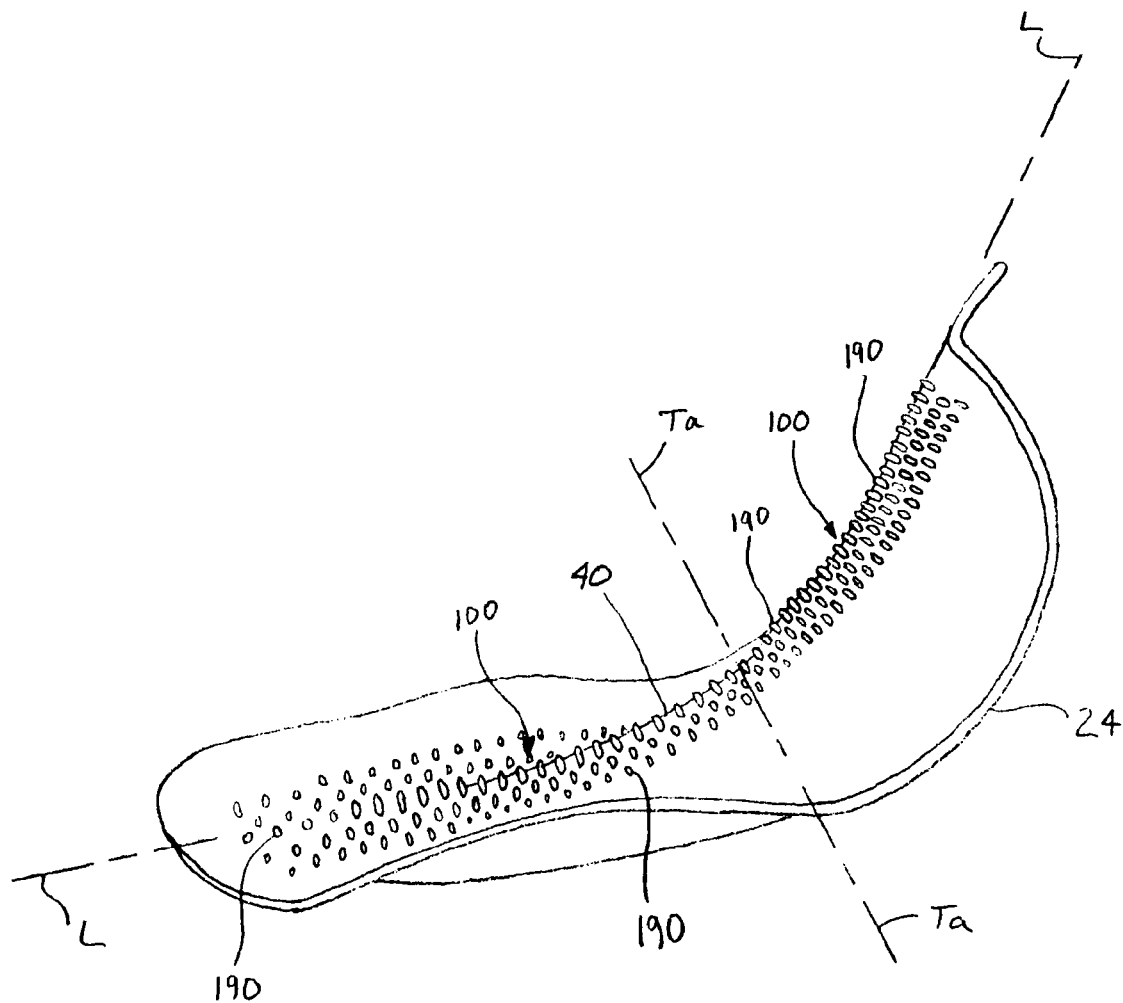
FIG. 17 is a schematic of an absorbent core having nodules.

FIG. 17 illustrates an absorbent core 24 in which a portion of the absorbent core 24 has a second compressibility in an altered state wherein the portion comprises nodules 190. As shown in FIG. 17, nodules 190 are portions of the absorbent core 24 deformed out of plane. Nodules 190 can be arranged in a staggered relationship with surrounding nodules 190. Without being bound by theory, it is thought that groups or fields of nodules 190 arranged in a staggered relationship can interact with one another and form a portion of the absorbent core 24 having a second compressibility in an altered state greater than the first compressibility in an unaltered state. Staggered, as used herein, means that the centroids of the portions deformed out of plane are placed on, or as if on, alternating sides of a line. The nodules 190 can be deformed out of plane of the absorbent core 24 in a direction towards the topsheet 21 or backsheet 22. Nodules 190 can coincide with discrete regions along the core longitudinal axis L of the absorbent core 24. Nodules 190 can be distributed over the entire absorbent core 24, with nodules 190 being spaced apart from one another.

Figure 18:
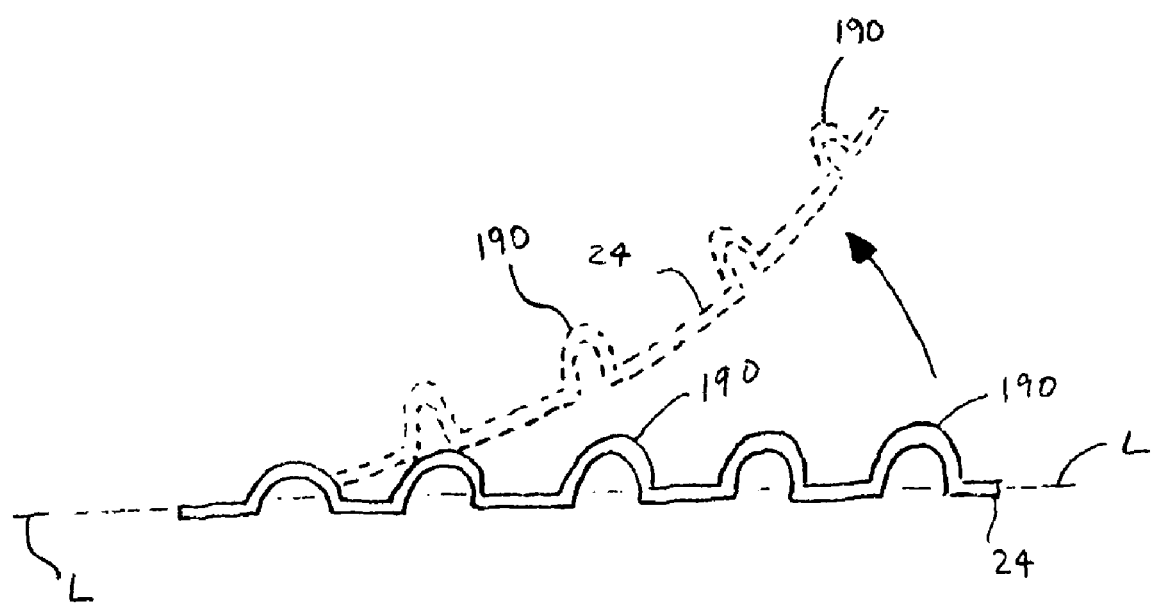
FIG. 18 is a schematic of the mechanical behavior of nodules.

A preferentially weakened zone of compression 100 can extend along the core longitudinal axis L, as shown in FIG. 17. The entire absorbent core 24 can comprise nodules 190 such that the portion of the absorbent core 24 having a second compressibility in an altered state can encompass the entire absorbent core 24. The absorbent core 24 comprising nodules 190 can be shortened along the core longitudinal axis L as the absorbent core 24 is bent about parallel axis Ta. Without being bound by theory, it is believed that nodules 190 can permit shortening of the absorbent core 24 because the portions of the absorbent core 24 deformed out of plane, which forms the nodule 190, can be weaker in compression as compared to the portions of the absorbent core between the nodules 190. As the absorbent core 24 is shortened along the core longitudinal axis L, the nodules 190 can be pushed further out of plane with respect to the portions of the core between the nodules 190 and the nodules 190 can partially fold up or partially close up upon themselves, as shown in FIG. 18. The nodules 190 can completely fold up or close up upon themselves. The compressibility of the portion of the absorbent core 24 having a second compressibility can be controlled by altering the spacing between individual nodules 190, the size of the nodules 190 in the plane of the absorbent core 24, and the amplitude by which the nodules 190 are pushed out of plane with respect to the plane of the absorbent core 24. The compressibility of the portion of the absorbent core 24 having a second compressibility can also be controlled by altering the geometry of the nodules 190.

Nodules 190 can be formed by a process commonly referred to as a "SELF" or "SELF'ing" process, in which SELF stands for Structural Elastic Like Film. The process was originally developed for deforming polymer films but can also be applied to nonwoven webs for absorbent cores, including air laid cores.

Figure 19:
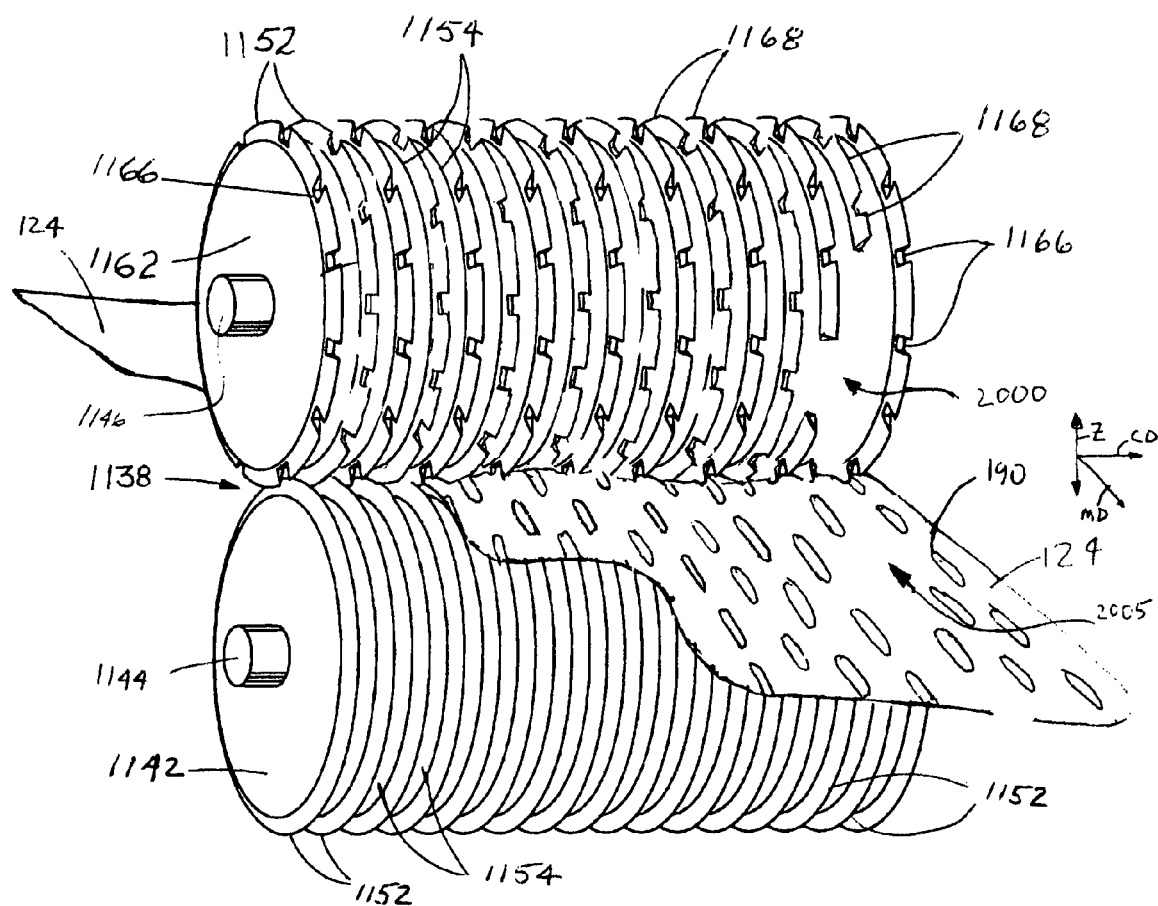
FIG. 19 is a schematic of a SELF'ing apparatus.

A configuration of opposed forming rolls for use in a SELF process is shown in FIG. 19. As shown in FIG. 19, an unmodified absorbent core web 124 can be fed from a supply roll into the nip 1138 of opposing forming roll 1142 and SELF roll 1162. The machine direction MD and cross direction CD are indicated in FIG. 19. Forming roll 1142 includes a plurality of circumferentially-extending, axially-spaced circumferential raised portions 1152 and grooves 1154 similar to forming rolls 1140 and 1142 described above. SELF roll 1162 includes a plurality of circumferentially-extending, axially-spaced circumferential raised portions 1152 wherein portions of the circumferential raised portions 1152 of SELF roll 1162 have been removed to form notches 1166 that define a plurality of circumferentially-spaced teeth 1168. Circumferentially-spaced teeth 1168 can be aligned with one another. Circumferentially-spaced teeth 1168 can be arranged in a staggered relationship, as shown in FIG. 19. Portions of SELF roll 1162 can be without teeth 1168 and/or portions of the forming roll 1142 can be without raised portions 1152 so as to permit undeformed portions 2005 of the absorbent core web 124 to be formed. Teeth 1168 can have a tooth height corresponding to raised portion height RH, and a tooth pitch corresponding to the pitch P, as illustrated in FIG. 16. The untooled region or regions 2000 of the SELF roll 1162, if present, can be circumferentially coordinated with an untooled region of the forming roll 1142. The portion or portions of the absorbent core 24 having nodules 190 can correspond with the portion or portions of the absorbent core 24 having a second compressibility.

As absorbent core web 124 passes through nip 1138, the teeth 1168 of SELF roll 1162 press a portion of absorbent core web 124 out of plane to cause permanent, localized Z-direction deformation of absorbent core web 124, the Z-direction being generally out of plane as compared to the generally planar configuration of absorbent core web 124. Portions of the absorbent core web 124 that pass between the notches 1166 of SELF roll 1162 and the teeth 1168 of SELF roll 1162 will be substantially unformed in the Z-direction, i.e., the absorbent core web 124 will not be deformed or stretched in that area to the same degree as that of the toothed regions, and can remain substantially planar, whereas portions of the absorbent core web passing between toothed regions of SELF roll 1162 and the raised portions 1152 of forming roll 1142 can be deformed or stretched beyond the elastic limit of the nonwoven, resulting in a plurality of deformed, raised, nodules 190 on the absorbent core web 124. If staggered circumferentially-spaced teeth 1168 are used on SELF roll 1162, nodules 190 can be formed in a staggered relationship.

Figure 20:
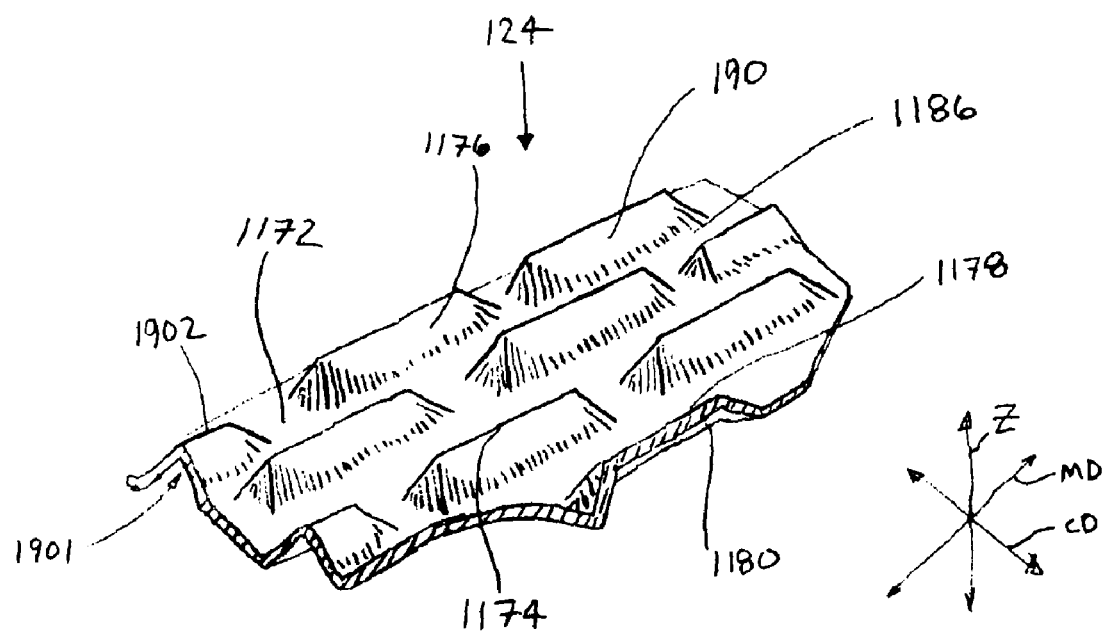
FIG. 20 is a schematic of an absorbent core having nodules.

A schematic representation of a portion of a SELF'ed absorbent core web 124 after it has passed between forming roll 1142 and SELF roll 1162 interengaged with one another and the rolls having the tooth configurations in which the circumferentially spaced teeth 1168 are staggered with respect to one another is illustrated in FIG. 20. SELF'ed absorbent core web 124 includes a network of distinct regions. The network can include at least a first region 1172, a second region 1174, and a transitional region 1176, which is at the interface between the first region 1172 and the second region 1174. SELF'ed absorbent core web 124 also has a first surface 1178 and an oppositely-facing second surface 1180. In the embodiment shown in FIG. 20, SELF'ed absorbent core web 124 includes a plurality of substantially flat, spaced first regions 1172 and a plurality of alternating nodules 190. The nodules 190 are comprised of tented portions 1901 of the absorbent core web 124. The tented portions 1901 can have a substantially angular apex 1902 (the apex being generally shaped like a tent having a triangular cross section), as shown in FIG. 20. The tented portions 1901 can have an approximately hemispherical shape, like a dome tent used for camping.

In the embodiment of FIG. 20, the second regions 1174 and intervening valleys 1186 are substantially linear, the second regions 1174 extending continuously in a direction substantially parallel to the direction in which the absorbent core web 124 passed though the nip 1138. In the embodiment of FIG. 20, the nodules have a longest dimension in a direction substantially parallel to the direction in which the absorbent core web 124 passed through the nip 1138. In the embodiment shown in FIG. 20, the first regions 1172 are not aligned with one another because the nodules 190 are staggered. Without being bound by theory, it is thought that arranging the nodules 190 in a staggered relationship that the nodules 190 can cooperate with adjacent nodules to provide enhanced compressibility.

In the embodiment shown in FIG. 20 first regions 1172 are substantially planar. That is, the material within first regions 1172 is substantially flat and is not altered substantially by passing between interengaged forming roll 1142 and SELF roll 1162.

In an air laid absorbent core 24, it has been found that the nodules 190 can be adjacent to one another and can be separated from each other by an unformed first region 1172 which can include the valleys 1186 separating adjacent nodules 190. Unformed first region 1172 can have a width between about 0.2 mm and about 3 mm as measured in the cross direction CD, as shown in FIG. 20. Unformed first region 1172 can have a width between about 2 mm and about 5 mm as measured in the machine direction MD, as shown in FIG. 20. The dimensions of the nodules 190 can also be varied, if desired.

Figure 21:
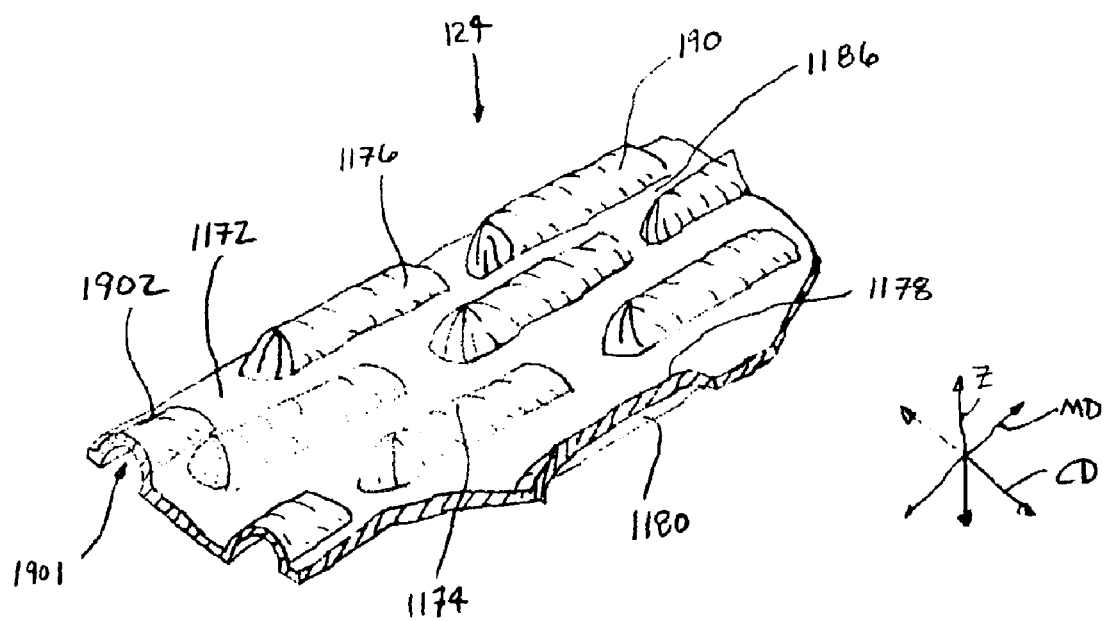
FIG. 21 is a schematic of an absorbent core having nodules.

The apex 1902 may be curved, as shown in FIG. 21 (the apex being generally shaped like a peak of a Quonset hut having a rounded apex).

Figure 22:
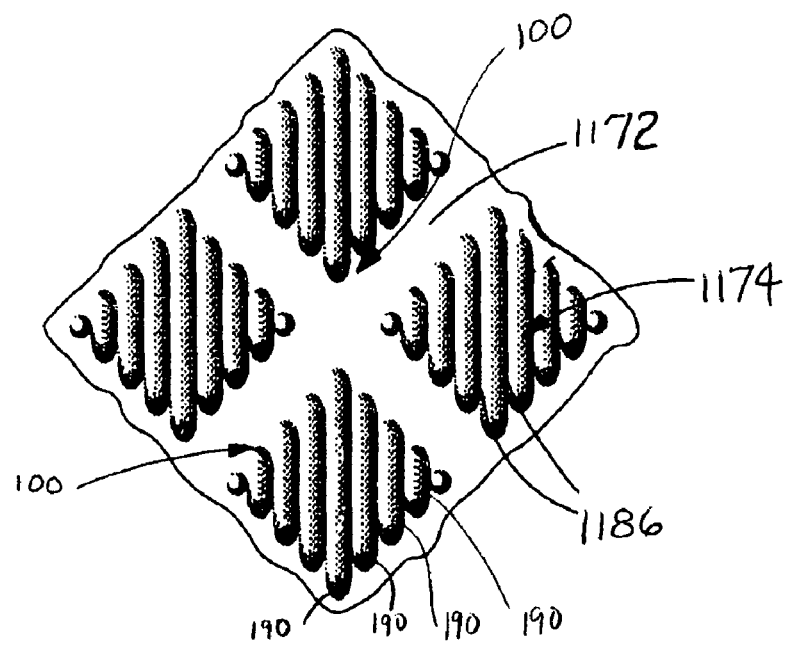
FIG. 22 is a schematic of an absorbent core having nodules.

In addition to the surface pattern illustrated in FIG. 20, a nonwoven web can be altered by other forming roll tooth and groove configurations that can cause localized stretching and/or deformation of the nonwoven material. For example, as shown in FIG. 22, the deformation pattern can be in the form of nodules 190 defining an array of spaced, diamond-shaped second regions 1174 with intervening undeformed first regions 1172. Each such diamond-shaped second region 1174 can be defined by alternating nodules 190 and intervening valleys 1186. Examples of methods and apparatus for formation of such diamond-shaped elements are disclosed in U.S. Pat. No. 5,650,214 and U.S. Pat. No. 6,383,431. As used herein, nodules 190 include rib-like elements, as disclosed in U.S. Pat. No. 5,650,214 and U.S. Pat. No. 6,383,431. Nodules can have an in-plane aspect ratio greater than or equal to about 1 in the plane of the absorbent core 24.

In one embodiment, diamond shaped second regions 1174 can be oriented such that the longer dimension of the nodules 190 are oriented substantially parallel to the core longitudinal axis L. In this arrangement, when the absorbent core 24 is bent along the longitudinal axis L, the nodules 190 can deform out of plane in a controlled manner to allow shortening of the absorbent core 24 along the core longitudinal axis.

Figure 23:
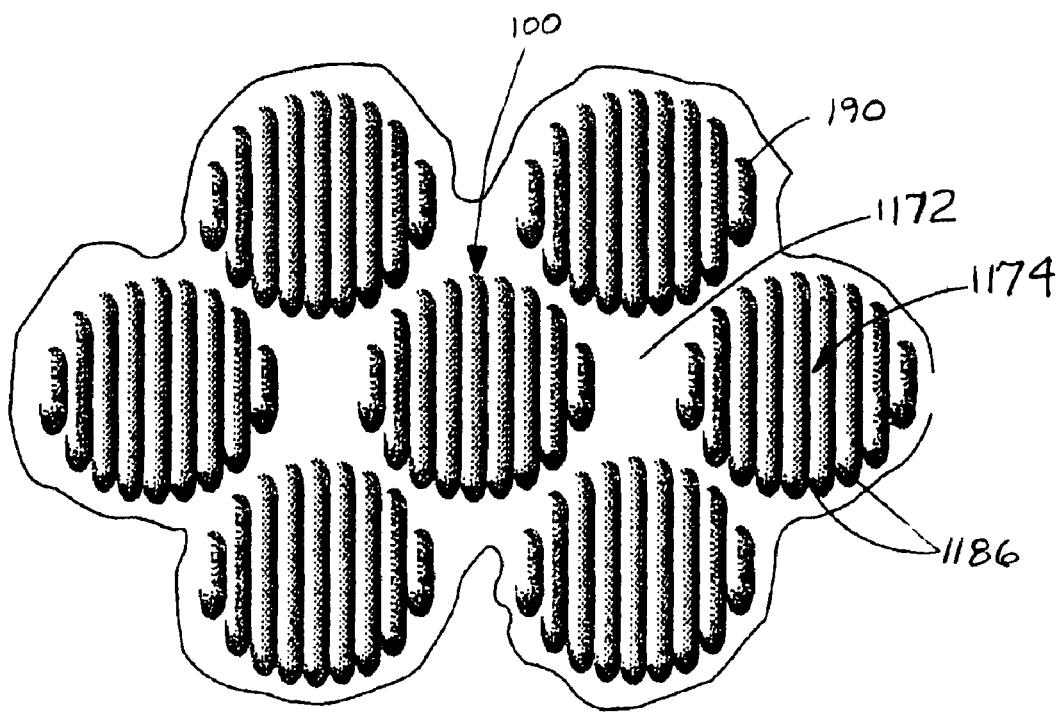
FIG. 23 is a schematic of an absorbent core having nodules.

As shown in FIG. 23, the deformation pattern can also be in the form of nodules 190 that together define an array of spaced, circularly-shaped second regions 1174. Each circular element can be defined by appropriately spaced, varying-length nodules 190 and intervening valleys 1186. Between respective circularly-shaped second regions 1174 are unformed intervening first regions 1172. Other deformation patterns can also be employed, if desired, such as those illustrated and described in U.S. Pat. No. 5,518,801.

For an absorbent core web 124 fed through the SELF'ing apparatus shown in FIG. 19, the core longitudinal axis L of the absorbent core 24 formed from the absorbent core web 124 can be generally orthogonal with the direction of travel so that the nodules 190 have a longer dimension in a direction substantially orthogonal to the core longitudinal axis L. Optionally, the core longitudinal axis L of the absorbent core 24 formed from the absorbent core web 124 can be substantially parallel with the direction of travel so that the nodules 190 have a longer dimension in a direction substantially parallel to the core longitudinal axis L. The core longitudinal axis L of the absorbent core 24 need not be substantially parallel or substantially orthogonal to the direction of travel such that a longer dimension of the nodules 190 is neither substantially parallel to the core longitudinal axis L nor substantially orthogonal to the core longitudinal axis L.

Oval shaped nodules 190 having a major axis of about 5 mm long and a minor axis of about 2 mm long can be practical. Nodules 190 can be spaced apart from each other along their major axes by about 3 mm and can be spaced apart from each other on their minor axes by about 1 mm to about 3 mm. Nodules 190 can be spaced apart from each other along their major axes by about 1 to about 3 mm and can be spaced apart from each other on their minor axes by about 1 mm to about 5 mm. Nodules 190 can be spaced apart from each other along their major axes by about 5 to about 8 mm and can be spaced apart from each other on their minor axes by about 5 mm to about 8 mm. Nodules having a longest dimension, in plan view, of less than about 10 mm can be practical. Nodules 190 in the absorbent core 24 can be pushed out of plane relative to the undeformed or lightly deformed portions of the absorbent core by about 0.8 mm.

Figure 24:
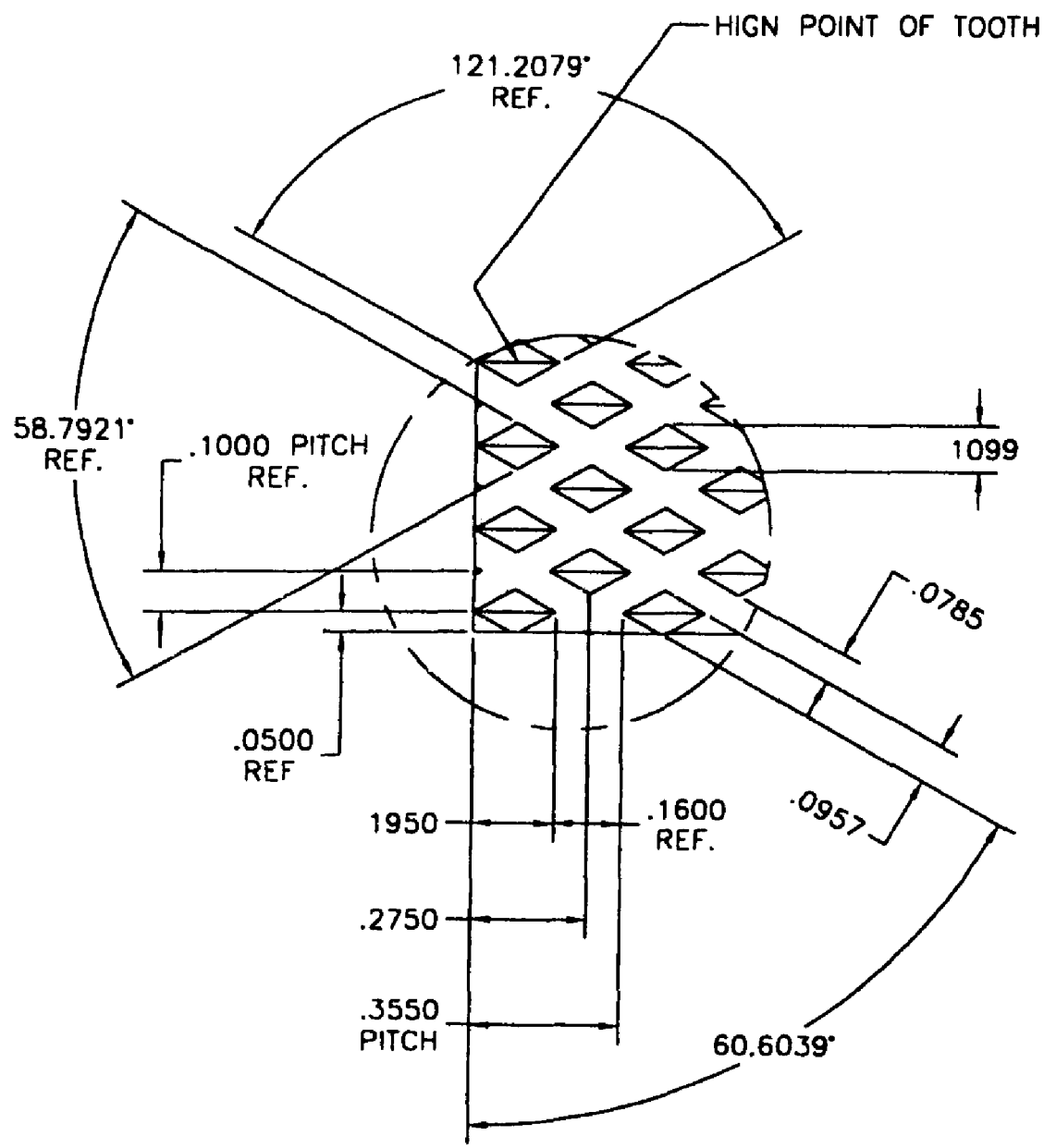
FIG. 24 is a schematic of a tooth pattern for a micro-SELF'ing apparatus.

FIG. 24 illustrates a tooth configuration that can be used in a SELF'ing process. The teeth, rather than having a generally rectangular shape when viewed from the top (i.e., in plan view, looking down on the surface of the roll), each tooth has a generally diamond shape as shown in FIG. 24 (the dimensions illustrated in FIG. 24 being in inches). Also, the pitch from tooth to tooth in a row can be 5.08 mm, which results in a 2.54 mm pitch from tooth to tooth in a staggered pattern. A staggered tooth pattern can result in nodules 190 that are staggered relative to one another, as shown in FIG. 20. The mating roll can be an un-toothed roll, that is, a roll having circumferentially extending ridges and grooves, similar to that shown in FIG. 19, wherein the two mating rolls can be meshed at a DOE of 1.78 mm. The SELF'ing process can be carried out at room temperature.

Figure 25:
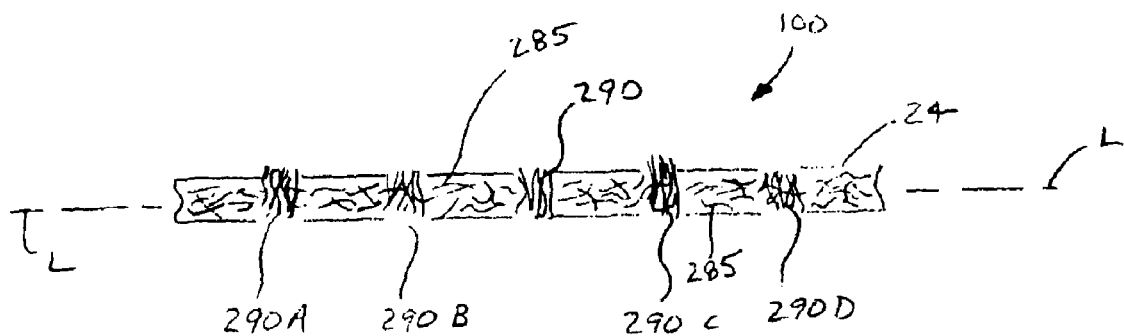
FIG. 25 is a schematic of an absorbent core having tufts.

FIG. 25 illustrates a cross section of an absorbent core 24 in which a portion of the absorbent core 24 has a second compressibility wherein the portion comprises tufts 290. For air-laid absorbent cores 24, the fibers comprising the absorbent core 24 are laid in a generally random structure. Tufts 290 are portions of the absorbent core 24 in which the fiber structure of the material is disturbed. That is, the interfiber boding of the fibers in the tuft 290 is reduced and/or weakened, as compared to portions of the absorbent core 24 without tufts 290. The orientation of fibers 285 in the tuft 290 can differ from the orientation of the fibers 285 in the portion of the absorbent core 24 without tufts 290 because the fiber structure is disrupted. In one embodiment, tufts 290 can comprise a plurality of fibers 285 having portions reoriented in a direction substantially orthogonal to the plane of the absorbent core 24.

In one embodiment of a tuft 290, in which a plurality of fibers 285 are reoriented in a direction substantially orthogonal to the plane of the absorbent core 24, the fraction of fibers 285 oriented orthogonal to the plane of the absorbent core 24 is greater in the tuft 290 than in adjacent non-tufted areas. In one embodiment, tufts 290 can comprise a plurality of fibers 285 having portions reoriented in a direction substantially orthogonal to the plane of the absorbent core and the reoriented fibers 285 are also pushed out of the plane of the absorbent core 24. The tufts 290 can be in plane with the absorbent core 24. The tufts 290 can coincide with discrete regions along the core longitudinal axis L of the absorbent core 24. The entire absorbent core 24 can comprise tufts 290 spaced apart from one another. An absorbent core 24 comprising tufts 290 can be shortened along the core longitudinal axis L as the absorbent core 24 is bent about parallel axis Ta. Without being bound by theory, it is believed that tufts 290 permit shortening of the absorbent core 24 because portions of the absorbent core 24 disturbed are weaker in compression as compared to the portion of the absorbent core between the tufts 290.

A plurality of tufts 290 can be grouped near one another to form a preferentially weakened zone of compression 100.

Figure 26:
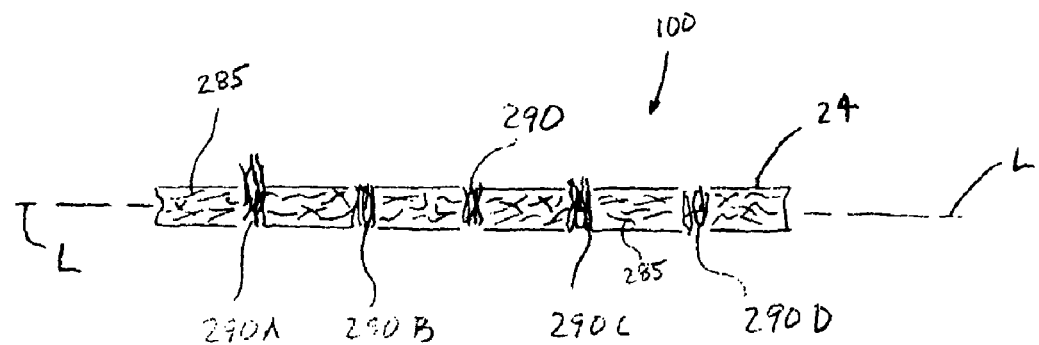
FIG. 26 is a schematic of an absorbent core having tufts.

As the absorbent core 24 is shortened along the core longitudinal axis L, the tufts 290 can move out of plane with respect to the portions of the core between the tufts 290 and/or the tufts 290 can collapse and/or compress, as shown in FIG. 26. For instance, tuft 290A shown in FIG. 25 compresses in the direction of the core longitudinal axis L and is pushed further out of the plane of the absorbent core 24 when absorbent core 24 is compressed in a direction along the core longitudinal axis L. Tufts 290B and 290C, as shown in FIG. 25, compress in the direction of the core longitudinal axis L when absorbent core 24 is compressed in a direction along the core longitudinal axis L. Tuft 290D, shown in FIG. 25, compresses in the direction of the core longitudinal axis L when absorbent core 24 is compressed in a direction along the core longitudinal axis L. The compressibility of the portion of the absorbent core 24 having a second compressibility and comprising tufts can be controlled by altering the spacing between individual tufts 290, the degree by which the tufts 290 are disturbed, and by altering the geometry of the tufts 290.

Figure 27:
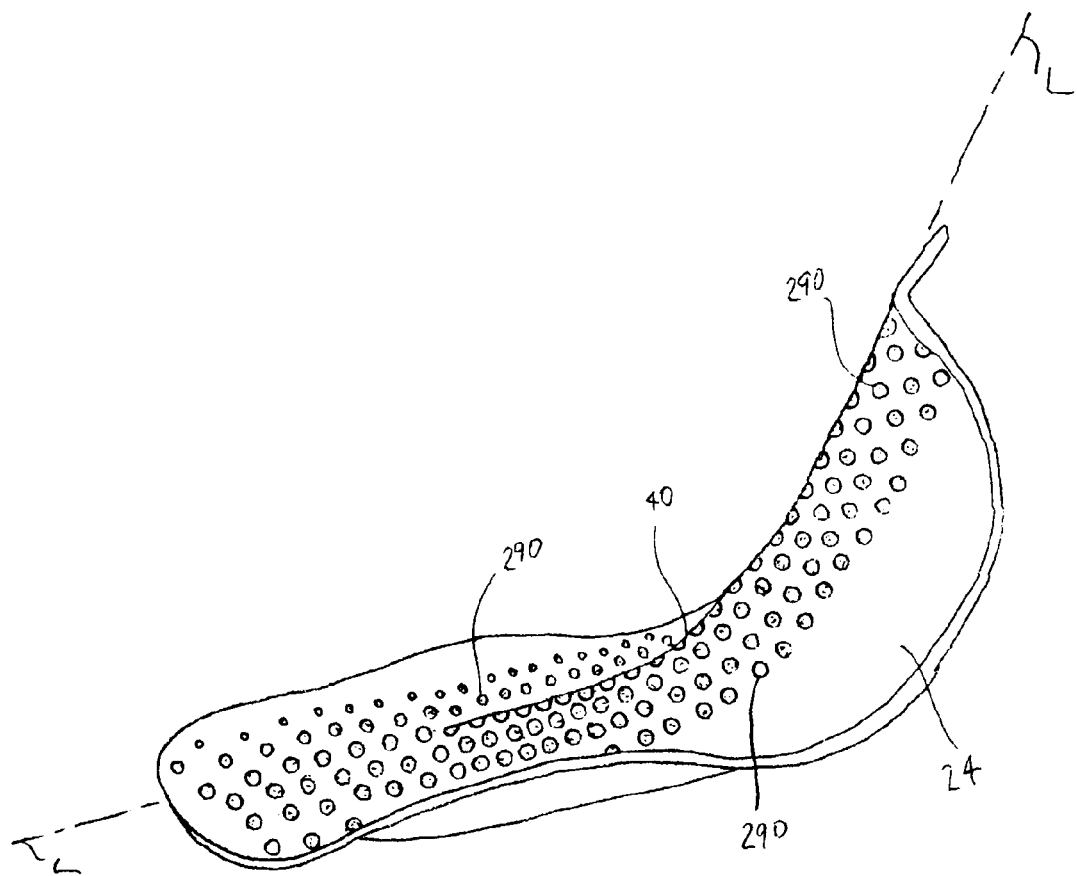
FIG. 27 is a schematic of an absorbent core having tufts.

FIG. 27 is a perspective view of a schematic of a portion of an absorbent core 24 comprising tufts 290. The portion(s) of the absorbent core 24 having a second compressibility can be preferentially weakened zone(s) of compression 100, as illustrated in FIG. 1. As shown in FIG. 27, the portion of the absorbent core 24 having a second compressibility can extend along the core longitudinal axis L. The entire absorbent core 24 can comprise tufts 290 such that portion of the absorbent core 24 having a second compressibility in an altered state can encompass the entire absorbent core 24.

Figure 28:
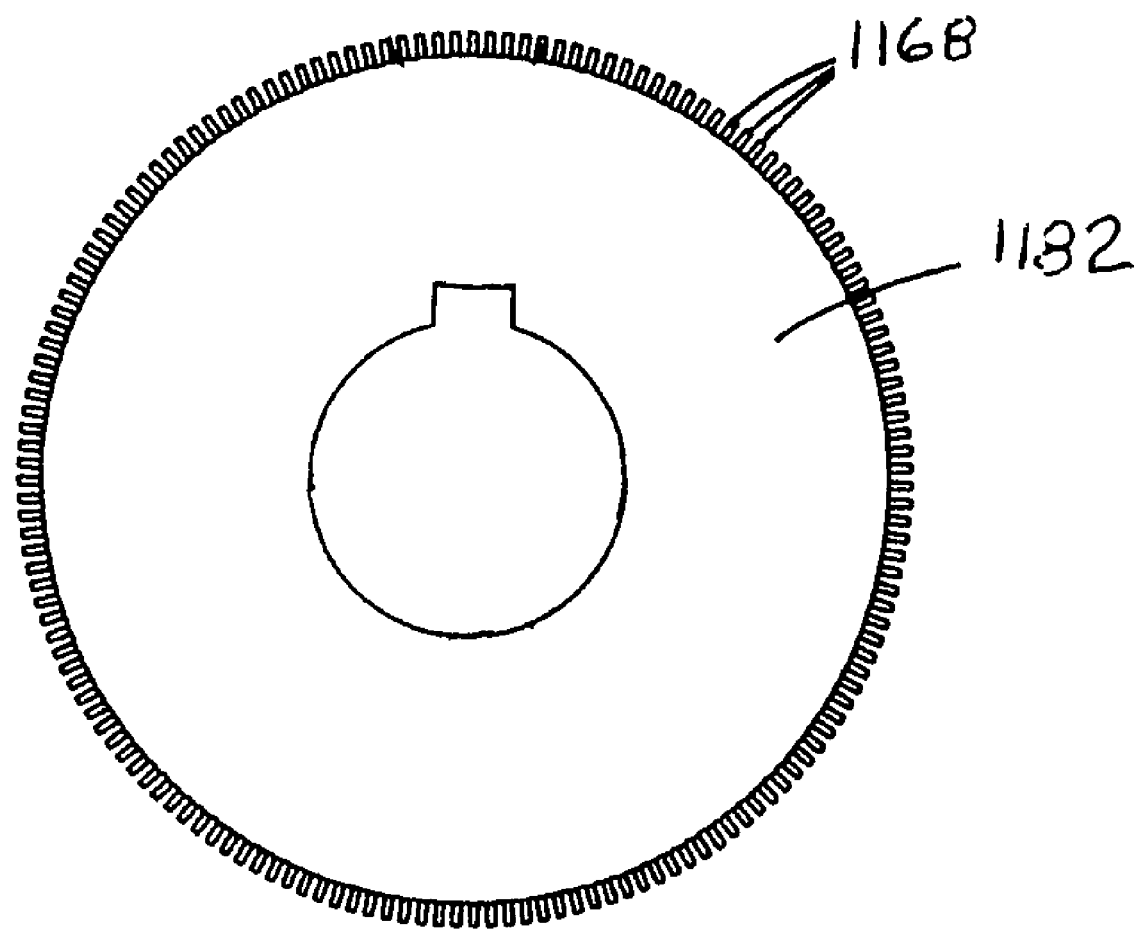
FIG. 28 is a schematic of a side view of a micro-SELF forming apparatus.

Tufts 290 can be created using a process described as "micro-SELF". Micro-SELF is a process that is similar in apparatus and method to that of the SELF process. The main difference between SELF and micro-SELF is the size and dimensions of the teeth 1168 on the toothed roll. The micro-SELF roll 1182, illustrated in FIG. 28, corresponds to SELF roll 1162 of FIG. 19. Referring to FIG. 28 there is shown a schematic side view representation of a micro-SELF roll 1182 that can be one of the rolls forming a nip roll arrangement in a configuration having one patterned roll, e.g., micro-SELF roll 1182. One non-patterned grooved roll similar to that shown as roll 1142 in FIG. 19 can be employed. Two interengaged micro-SELF rolls 1182 having either the same or differing patterns, in the same or different corresponding regions of the respective rolls can be used. In the micro-SELF roll of FIG. 29, individual teeth 1168 can have a tooth length TL of about 1.27 mm with a distance between teeth TD of about 1.57 mm and a pitch of about 1.52 mm. In one embodiment, the circumference of micro-SELF roll 1182 can be such that there are 158 teeth 1168 separated by 159 cuts between teeth 1168. Portions of micro-SELF roll 1182 can be without teeth 1168 to permit forming of absorbent cores 24 having portions without tufts 290 and portions with tufts 290. The portions with tufts 290 can correspond to the portion of the absorbent core 24 that has a second compressibility.

Figure 29:
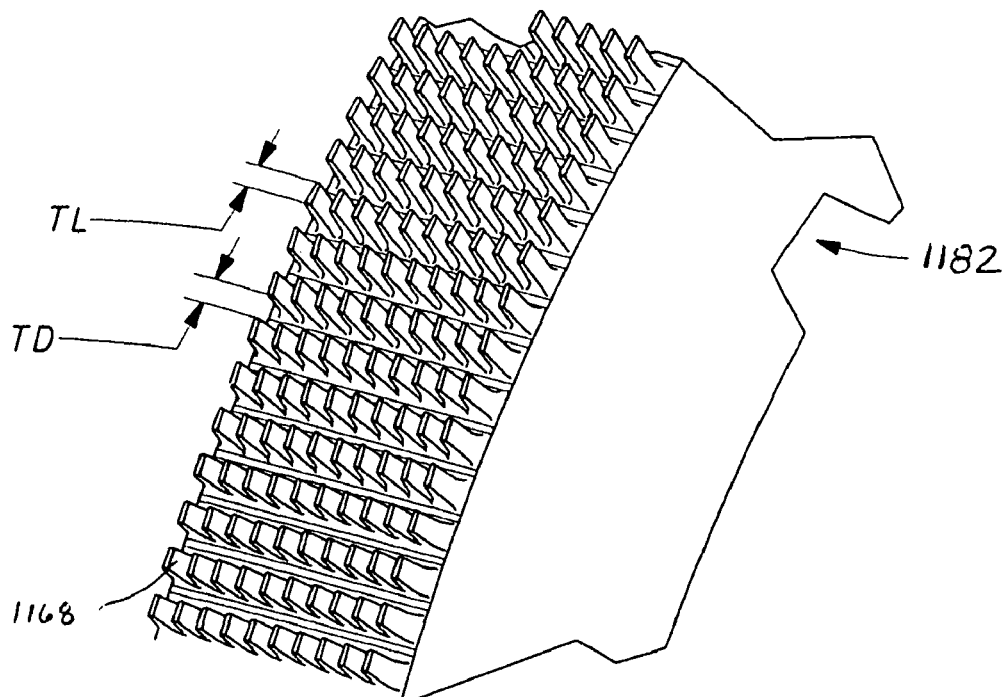
FIG. 29 is a schematic of a tooth pattern for a micro-SELF forming roll.
Figure 30:
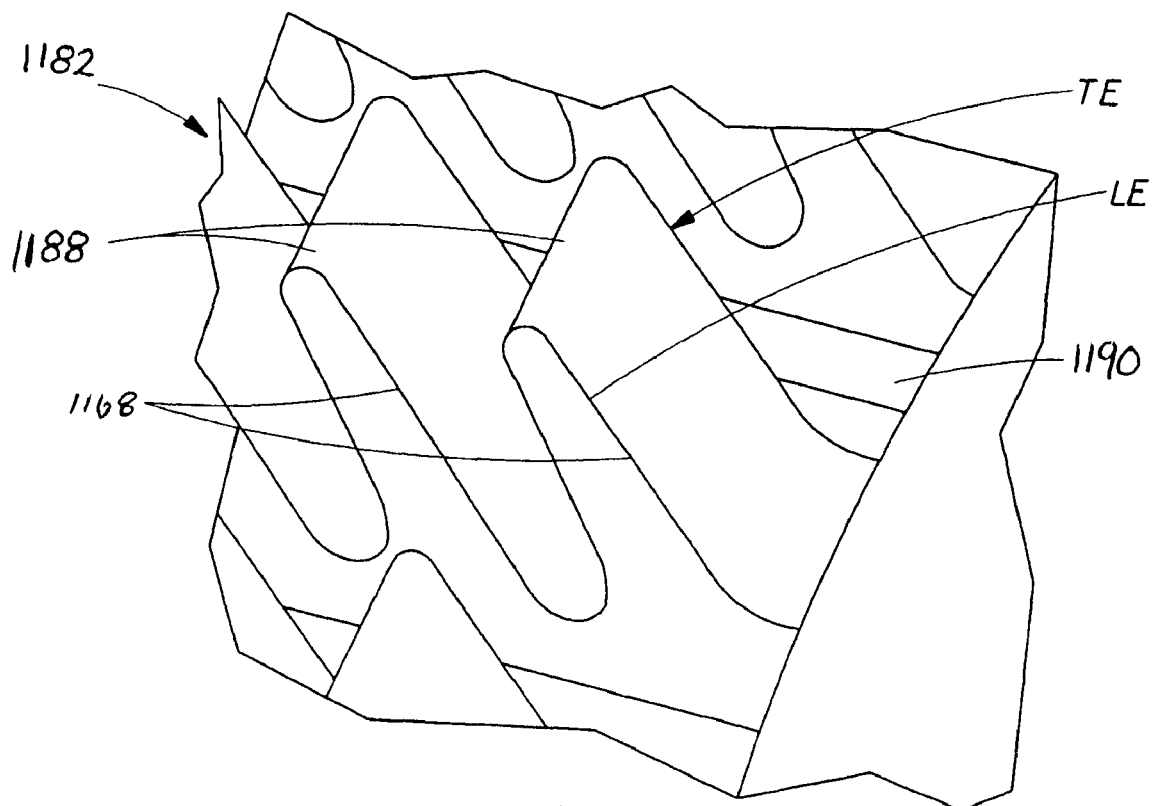
FIG. 30 is a schematic of a tooth arrangement for a micro-SELF forming roll.

As shown in the partial perspective view of FIG. 29 and the enlarged partial perspective view of FIG. 30, the teeth 1168 of a micro-SELF roll 1182 have a specific geometry associated with the leading and trailing edges of teeth 1168 that permit the teeth to essentially "punch" through the absorbent core web 124 as opposed to, in essence, deforming the web into nodules, bumps, or ridges as shown in FIGS. 12, 13, 14, 17, 18, 20, and 21. In some embodiments of an absorbent core web 124 suitable for use in an absorbent core 24, the teeth 1168 urge fibers out-of-plane to form tufts having looped fibers. Unlike the nodules 190 of SELF webs, which each have continuous side walls associated therewith, i.e., a continuous "transition zone," the tufts 290 can have a discontinuous structure associated with the side wall portions of the Z-direction deformations. Additionally, when used for relatively high basis weight absorbent core materials, the "tufting" can be somewhat invisible as fibers are urged out of the plane in a Z-direction with respect to one of the web surfaces, the Z-direction deformation may be muted or non-existent in the other web surface. Further, when a laminate material is involved, the Z-direction deformations of one web material may be pushed into and "hidden" by the second material of the laminate, such that the "tufting" is essentially invisible to the naked eye.

As shown in FIGS. 29 and 30, each tooth 1168 has a tooth tip 1188, a leading edge LE and a trailing edge TE. The tooth tip 1188 is elongated and has a generally longitudinal orientation. It is believed that to get tufts 290 having looped fibers the LE and TE should be very nearly orthogonal to the local peripheral surface 1190 of micro-SELF roll 1182. As well, the transition from the tooth tip 1188 and LE or TE should be a sharp angle, such as a right angle, having a sufficiently small radius of curvature such that teeth 1168 push through absorbent core web 124 at the LE and TE. Without being bound by theory, it is believed that having relatively sharply angled tip transitions between the tip of tooth 1168 and the LE and TE permits the teeth 1168 to punch through the absorbent core web 124 "cleanly", that is, locally and distinctly, so that the resulting web can be described as "tufted" or otherwise "deformed."

The teeth 1168 of a micro-SELF roll 1182 can have a uniform circumferential length dimension TL measured generally from the leading edge LE to the trailing edge TE at the tooth tip 1188 of about 1.25 mm and can be uniformly spaced from one another circumferentially by a distance TD of about 1.5 mm. For making an absorbent core web 124 from absorbent core web 124 having a total basis weight in the range of about 60 to about 100 gsm, teeth 1168 of micro-SELF roll 1182 can have a length TL ranging from about 0.5 mm to about 3 mm and a spacing TD from about 0.5 mm to about 3 mm, a raised portion height RH, corresponding to the tooth height, ranging from about 0.5 mm to about 5 mm, and a pitch P between about 1 mm and about 5 mm. Depth of engagement E can be from about 0.5 mm to about 5 mm (up to a maximum equal to the raised portion height RH). Of course, E, P, RH, TD, and TL can be varied independently of each other to achieve a desired size, spacing, and area density of web deformations.

The disclosures of the patent applications filed in the United States Patent and Trademark Office on Mar. 5, 2007, in the name of Zhao et al., titled "Disposable Absorbent Article", "Absorbent Core for Disposable Absorbent Article", and "Absorbent Core for Disposable Absorbent Article" also disclose various solid state formation techniques for absorbent cores.

In one embodiment, the each tuft 290 can have a maximum dimension measured in the longitudinal direction of the absorbent core 24 that can be about 1 mm to about 6 mm. The maximum dimension of each tuft 290 measured in the longitudinal direction of the absorbent core 24 can be between about 2 mm and about 5 mm. The tufts 290 can be spaced apart from one another by about 0.01 mm to about 10 mm. The tufts 290 can be spaced apart from one another by about 0.5 mm to about 5 mm. The tufts 290 can be spaced apart from one another by about 3 mm to about 5 mm. The tufts 290 can be spaced apart from one another by about 2 mm.

Nodules 190 and tufts 290 can have a maximum dimension in the plane of the absorbent core 24 (the plane defined by the core longitudinal axis L and a transverse axis orthogonal to the core longitudinal axis L and parallel to the transverse axis T). Nodules 190 and tufts 290, as well as other structural features, can be spaced apart from one another by a distance less than maximum dimension. Nodules 190 and tufts 290, as well as other structural features, can be spaced apart from one another by a distance less than about 50% of the maximum dimension. Nodules 190 and tufts 290, as well as other structural features, can be spaced apart from one another by a distance less than about 10% of the maximum dimension.

The portion of the absorbent core 24 that has a second compressibility can comprise structural features selected from the group consisting of slits 110, corrugations 180, nodules 190, and tufts 290. A preferentially weakened zone of compression 100 can comprise structural features selected from the group consisting of slits 110, corrugations 180, nodules 190, and tufts 290. A portion of the absorbent core that is generally aligned with the core longitudinal axis can comprise structural features selected from the group consisting of slits 110, corrugations 180, nodules 190, and tufts 290, as shown herein, to allow the core the deform into the desired shape.

An elastic member 200 can be added to the feminine hygiene device 20 to assist with creating the complex three dimensional shape of the feminine hygiene device 20. The elastic member 200 can span at least a portion of the absorbent core 24 comprising a preferentially weakened zone of compression 100. The elastic member 200 can span at least a portion of the absorbent core 24 having the second compressibility. The elastic member can span at least a portion of the absorbent core 24 comprising the previously described structural features. The elastic member 200 can be generally aligned with the core longitudinal axis L. The elastic member 200 can be located between the absorbent core 24 and the backsheet 22. Each end of the elastic member 200 can be attached or joined to either the absorbent core 24 or the backsheet 22 or can be attached or joined to both the absorbent core 24 and the backsheet 22. The absorbent core 24 can be attached or joined to the backsheet 22. More than one elastic member 200 can be added to the feminine hygiene device 20. The elastic member 200 can be adjacent the backsheet 22. The majority of the absorbent material (by mass or volume) can be located between the elastic member 200 and the topsheet 21.

The elastic member 200 can be operatively related to the absorbent core 24. By operatively related, it is meant that force from the elastic member 200 in a stretched condition can be transmitted to the absorbent core 24 to assist the absorbent core 24 in obtaining the desired shape. Force from the elastic member 200 can be transferred directly to the absorbent core 24 by joining the elastic member 200 to the absorbent core 24 or by joining the elastic member 200 to the backsheet 22, at least a portion of the backsheet 22 being joined to a portion or portions of the absorbent core 24. The elastic member 200 can be joined to both the absorbent core 24 and the backsheet 22.

When more than one elastic member 200 is used, each elastic member 200 can have the same length, cross-section, and elastic properties. Each elastic member 200 can have different length, cross-section, and elastic properties. When more than one elastic member 200 is used, some of the elastic members 200 can be the same as other elastic members 200 and different from other elastic members 200. For instance, the feminine hygiene device 20 can have a first elastic member 200 having one set of properties and a pair of second elastic members 200 having another set of properties, properties including, but not limited to, length, cross-section, and elastic properties.

Elastic member 200 can be a strand of elastic material. The length of the elastic member 200 is the longest dimension of the elastic member 200. Because the elastic member 200 is elastic, the length of the elastic member 200 is a function of the tension in the elastic member. The cross section of the elastic member 200 can be circular, oval, rectangular, square, polygon, or irregular. The cross section of the elastic member 200 can vary along the length of the elastic member 200.

Elastic member 200 can provide for about 15 mm to about 50 mm of contraction with a contractive force of about 0.39 N to about 0.981 N. In one embodiment, elastic member can provide for about 10 mm to about 50 mm of contraction, and the contractive force can be about 0.49 N to about 0.59 N. In one embodiment, the elastic member can be about 140 mm long and provide for a stretch of about 30 mm at a force between about 0.88 N and about 0.98 N. In one embodiment, the elastic member can be about 160 mm long and provide for a stretch of about 30 mm at a force between about 0.88 N and about 0.98 N. In one embodiment, the elastic member 200 can provide elastic elongation between about 15% and about 26%, the elastic elongation can be between about 25 mm and about 30 mm, and the stretching force can be between about 0.39 N and about 1.47 N.

Elastic member 200 can be STRETCHRITE® soft stretch elastic about 3 mm wide available from Rhode Island Textile Co. of Pawtucket R.I. When the feminine hygiene device 20 is packaged in a generally flat and unfolded condition, elastic member 200 can be in a stretched position. Upon removal from the package and/or when worn, elastic member 200 can contract, causing the absorbent core 24 to shorten in the portion(s) having the second compressibility. The contraction of elastic member 200 generally along the core longitudinal axis L, as shown in FIG. 3, tends to draw the absorbent core into a more defined and stable inverted V-shape in the rear portion of feminine hygiene device 20.

Topsheet 21 can comprise fibrous nonwoven materials comprised of fibers known in the art including bicomponent and/or shaped fibers. Bicomponent fibers can comprise polypropylene (PP) and polyethylene (PE) in known configurations, including core/sheath, side by side, islands in the sea, or pie shaped. The topsheet 21, or portions thereof, can be extensible. The topsheet 21 can comprise an apertured polymer film marketed under the trade name DRI-WEAVE® by The Procter & Gamble Co., Cincinnati, Ohio, or an apertured formed film.

Backsheet 22 can comprise any of the materials known in the art for backsheets, such as polymer films and film/nonwoven laminates. To provide a degree of softness and vapor permeability for the garment-facing side of feminine hygiene device 20, backsheet 22 can be a vapor permeable outer layer on the garment-facing side of the feminine hygiene device 20. The backsheet 22 can be formed from any vapor permeable material known in the art. Backsheet 22 can comprise a microporous film, an apertured formed film, or other polymer film that is vapor permeable, or rendered to be vapor permeable, as is known in the art. One suitable material is a soft, smooth, compliant, vapor pervious material, such as a nonwoven web that is hydrophobic or rendered hydrophobic to be substantially liquid impermeable. A nonwoven web provides for softness and conformability for comfort, and can be low noise producing so that movement does not cause unwanted sound.

Other materials and components of feminine hygiene devices 20 are contemplated to be within the scope of the description, including those disclosed in U.S. Pat. No. 4,950,264 issued to Osborn III Aug. 21, 1990 and U.S. Pat. No. 5,439,458 issued to Noel et al. Aug. 8, 1995.

The absorbent core 24, and backsheet 22 can comprise absorbent materials, and liquid impermeable film materials, respectively, as is well known in the art. Side extensions 28, e.g., wings, if used, can be integral extensions of the topsheet 21 or the backsheet 22 or both, and they can be symmetric about the longitudinal axis FL, transverse axis T, or both. The topsheet 21 and backsheet 22 can be joined to one another by adhesive bonding, thermal bonding, ultrasonic bonding, compression bonding, and the like.

Nonwoven webs used in the present invention can be any known nonwoven webs or composites of two or more nonwoven webs. Nonwoven webs used in the present invention can comprise fibers that are monocomponent, bicomponent, biconstituent, capillary channel fibers, or combinations thereof.

The topsheet 21 and the absorbent core 24 can be joined by any means known in the art including adhesive bonding, thermal bonding, ultrasonic bonding, compression bonding, and the like. In one embodiment contemplated, the topsheet 21 and absorbent core 24 are joined in only selected regions.

The compressibility of portions of the components of feminine hygiene device 20, including preferential zones of compression 100 in the absorbent core 24, can be determined by any of many means well-known in the art. For instance, the relative compressibility of a material in an unaltered state as compared to the compressibility in an altered state can be inferred by one skilled in the art by looking at how the material is altered and thinking about how the material that is altered will behave in compression as compared to how an unaltered material will behave in compression.

Although not necessary for one skilled in the art to determine the relative compressibility of a material in an unaltered state as compared to the compressibility in an altered state, a mechanical compression testing device, such as an MTS machine, can be employed to make the evaluation. A test specimen can be a generally rectangular prismoidal shape can have a length to width ratio of about 2 (the length being the longest dimension, the width being the second longest dimension, and the thickness being the smallest dimension, wherein the thickness is less than about 1/10 the width). The test specimen can be folded in half (lengthwise) such that the folded test specimen has a length to width ratio of 4 and then opened such that the angle subtended by the test specimen is 160° and leaving a length-wise fold line. Load can be applied to each end of the test specimen by circular loading plates having a diameter of 1/10 of the width of the test specimen, the loading plates being aligned with the fold line such that the loading plates are centered on the fold line. Other technical approaches for measuring the compressibility are possible keeping in mind that the compressibility of the absorbent core along the core longitudinal axis is of interest and that the in-use condition of the absorbent core can be such that the absorbent core has a ridge along a portion of the absorbent core generally aligned with the core longitudinal axis.

It is implied herein that measurements are to be made at relatively low strains from about 0.1% to about 10%, and at appropriate rates of strain representative of in use conditions. By way of example, an appropriate rate of strain is defined as anything from 100% strain in about 2 seconds to 100% strain in about 3 minutes. Compressibility can be quantified in terms of modulus and/or force required for a particular deformation, with greater compressibility associated with materials having a lower modulus or less force required to produce a particular deformation. For a given strain of between about 0.1% to about 10%, the ratio of the modulus (slope of stress to stain curve), as measured in compression, of the portion of the absorbent core 24 having a second compressibility to the modulus of the portion of the absorbent core 24 having the first compressibility can be less than 1 (but greater than 0). For a given strain of between about 0.1% to about 10%, the ratio of the modulus, as measured in compression, of the portion of the absorbent core 24 having a second compressibility to the modulus of the portion of the absorbent core 24 having the first compressibility can be between about 0.01 and about 0.99, an any dimensions there between in increments of 0.01 from these values. The above ratios are also applicable to force required to produce a particular deformation.

For a given strain of between about 0.1% to about 10%, the ratio of the modulus, as measured in compression, of the portion of the absorbent core 24 having a second compressibility to the modulus of the portion of the absorbent core 24 having the first compressibility can be between about 0.1 and about 0.9, an any dimensions there between in increments of 0.1 from these values. For a given strain of between about 0.1% to about 10%, the ratio of the modulus, as measured in compression, of the portion of the absorbent core 24 having a second compressibility to the modulus of the portion of the absorbent core 24 having the first compressibility can be less than about 0.5 (but greater than 0). The above ratios are also applicable to force required to produce a particular deformation.

Joining of the absorbent core 24 and the backsheet 22 can be by any means known in the art, such as by adhesive bonding, thermal bonding, ultrasonic bonding, and the like. Although complete bonding at interface is not necessary, it is believed that the bonding should be sufficient to facilitate the components to act as a unit, e.g., bending out-of-plane together upon sufficient lateral force. In one embodiment, the absorbent core 24 is adhered to the body-facing side of the backsheet 22 at generally the entire surface interface between the two components, e.g., by the use of meltblown thermoplastic adhesive. Adhesion can be by application of a generally uniform layer of adhesive applied by means known in the art, such as by spraying or slot coating. The adhesive can be a fluid permeable adhesive, such as Findley HX1500-1 adhesive.

Figure 31:
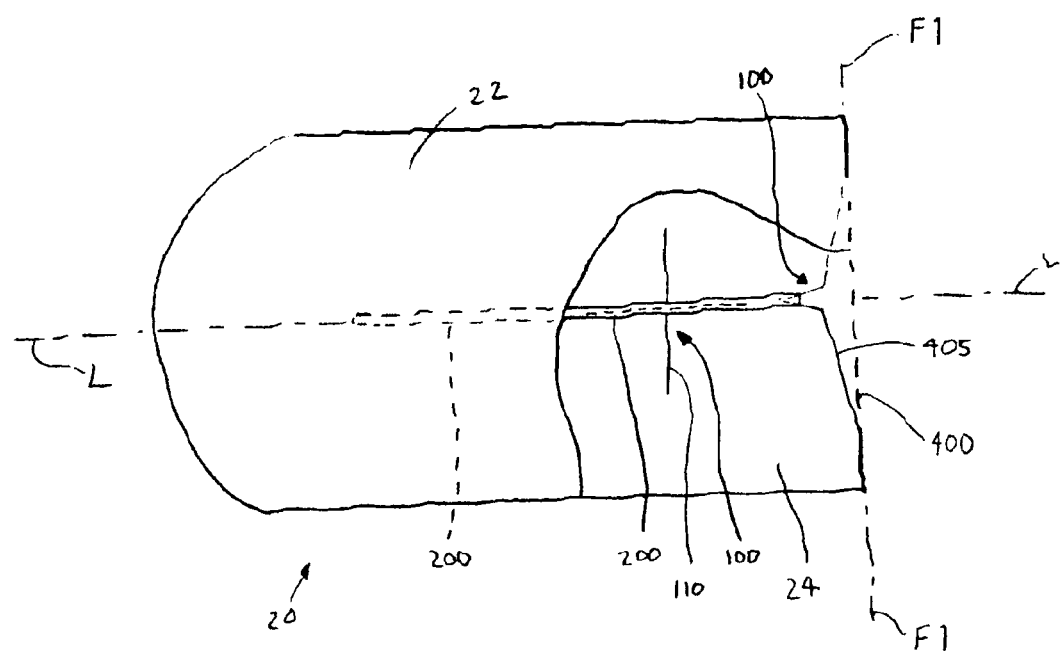
FIG. 31 is a schematic of a folded feminine hygiene article.

The feminine hygiene device 20 disclosed herein can also be folded flat to permit convenient packaging. As shown in FIG. 31, the feminine hygiene device 20 can have a first folding axis F1 that can be generally orthogonal to the core longitudinal axis L. The feminine hygiene device 20 can be folded generally flat about the first folding axis F1 to form an absorbent core first fold line 405 and a feminine hygiene device first fold line 400. A portion of the absorbent core first fold line 405 can be proximal to a portion of the absorbent core 24 having a second compressibility. That is, the absorbent core first fold line 405 can be close enough to a portion of the absorbent core 24 having a second compressibility so that the portion can be compressed longitudinally upon folding. In an unfolded position, the elastic member 200 can be in tension. As the feminine hygiene device 20 is folded about the first folding axis F1, the portion of the absorbent core 24 having a second compressibility can allow the absorbent core 24 to shorten along the core longitudinal axis L and/or deform along the absorbent core first fold line 405. The shape of the absorbent core first fold line 405 can differ from the feminine hygiene device first fold line 400. If the absorbent core 24 and backsheet 22 are joined to one another along the first folding axis then F1 can be non-linear (i.e. may be slightly curved or irregular and not a straight line). Similarly, if the elastic member 200 is joined to the backsheet 22 near the first folding axis F1, the first folding axis F1 may be slightly curved or irregular and not a straight line.

The tension in the elastic member 200 in the folded position can be less than the tension in the elastic member 200 in the unfolded position. The tension in the elastic member 200 in the folded position can be less than the tension in the elastic member 200 in the unfolded position because the absorbent core 24 can shorten along the core longitudinal axis L and/or deform along the absorbent core first fold line 405. Given that length of the elastic member 200 is functionally related to tension in the elastic member, the length of the elastic member 200 when the feminine hygiene device 20 is in a folded position can be less than the length of the elastic member 200 when the feminine hygiene device 20 is in an unfolded position.

Having the tension in the elastic member 200 in the folded position less than the tension in the unfolded position can reduce the tendency for the elastic member 200 to creep during long-term storage in a folded position. Furthermore, reducing the tension in the elastic member 200 when the feminine hygiene device 20 is in a folded position limits the tendency for the folded feminine hygiene device 20 to "explode" like a jack in the box when the folded feminine hygiene device 20 is removed from a package containing multiple feminine hygiene devices 20. Rather, the tendency of the folded feminine hygiene device 20 is to remain in a partially folded position when removed from a package containing multiple feminine hygiene devices 20, which makes the feminine hygiene device 20 easy for user to handle and place in her panty. As the user unfolds the feminine hygiene device 20, tension in the elastic member 200 is mobilized and the feminine hygiene device 20 takes the three-dimensional shape illustrated in FIG. 3.

The length of the absorbent core first fold line 405 can be greater than the width of the absorbent core 24 away from the first folding axis F1. The elastic member 200 can span at least a portion of the absorbent core 24 having a second compressibility and is generally aligned with the longitudinal axis FL. As shown in FIG. 31, the elastic member 200 can cause the absorbent core 24 to shorten along the core longitudinal axis L and deform along the absorbent core first fold line 405. Thereby, the absorbent core first fold line 405 is deformed away from the first folding axis F1 and the length of the absorbent core first fold line 405 can be greater than the width of the absorbent core 24 away from the first folding axis F1. If the absorbent core 24 and backsheet 22 are joined to one another along the first folding axis F1, the first folding axis F1 may be slightly curved or irregular and not a straight line. Similarly, if the elastic member 200 is joined to the backsheet 22 near the first folding axis F1, the first folding axis F1 may be slightly curved or irregular and not a straight line.

Figure 32:
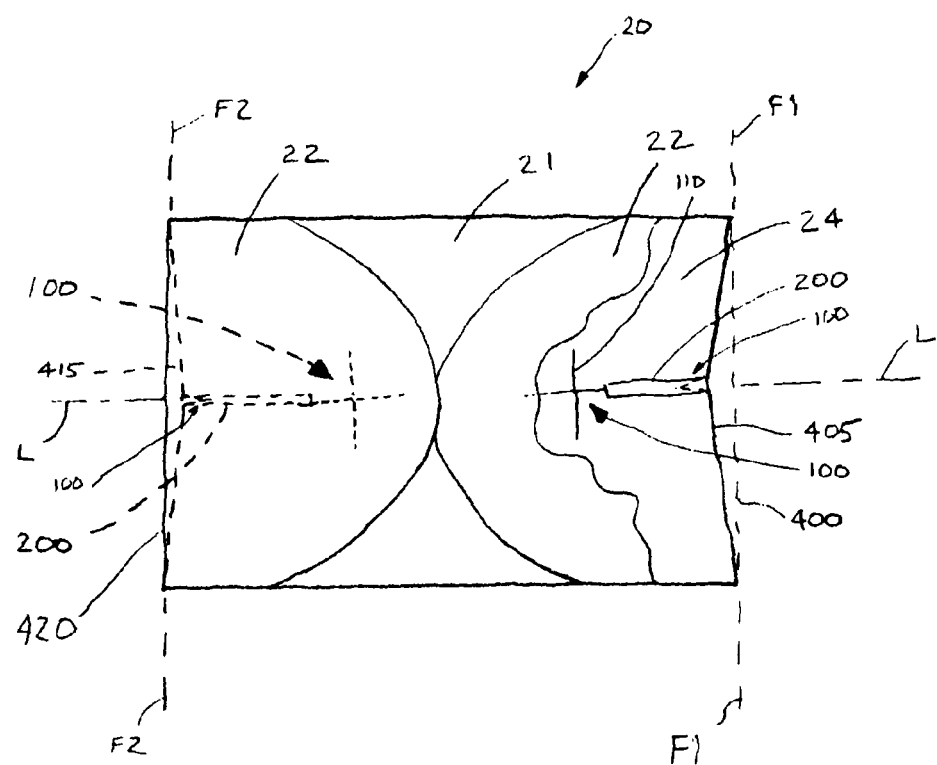
FIG. 32 is a schematic of a folded feminine hygiene article.

As shown in FIG. 32, the feminine hygiene device 20 can be folded flat about a second folding axis F2 to form a feminine hygiene device second fold line 420 and an absorbent core second fold line 415. Similar to the first folding axis F1, the second folding axis F2 can be generally orthogonal to the absorbent core longitudinal axis L. A portion of the absorbent core second fold line 415 can be proximal to a portion of the absorbent core 24 having a second compressibility.

Figure 33:
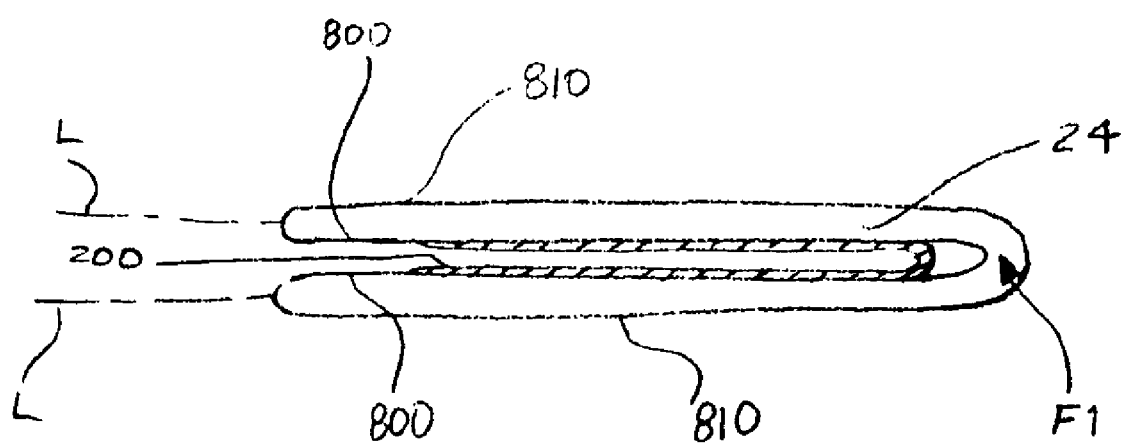
FIG. 33 is a schematic of a folded absorbent core.

As shown in FIG. 33, the absorbent core 24 can be considered to have a first side 800 and a second side 810. The elastic member 200 can be disposed on the first side 800 of absorbent core 24. The first side 800 of absorbent core 24 can be the garment facing side of the absorbent core 24. The second side 810 of the absorbent core 24 can be the body facing side of the absorbent core 24. The feminine hygiene device 20 can be folded upon itself such that the feminine hygiene device has a first folding axis F1 that is generally orthogonal to the core longitudinal axis L. The feminine hygiene device 20 can be folded flat about the first folding axis F1 such that the first side 800 of the absorbent core 24 is folded upon itself. That is, the feminine hygiene device 20 can be folded such that that the absorbent core 24 is folded so that portions of the first side 800 of absorbent core 24 face one another and the elastic member 200 is sandwiched there between.

Figure 34:
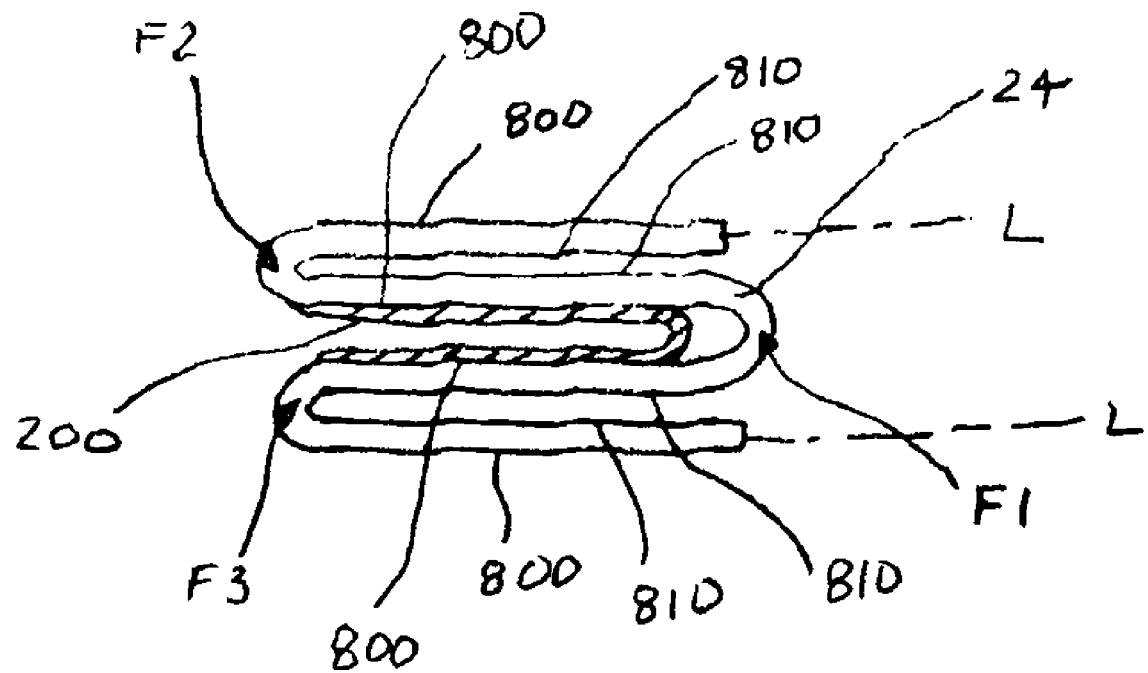
FIG. 34 is a schematic of a folded absorbent core.

As shown in FIG. 33, the elastic member 200 can be folded at a different location than where the absorbent core 24 is folded. By folding the absorbent core 24 in this manner, stress in the elastic member 200 in the folded position can be less than the stress in the elastic member 200 in the unfolded position. As shown in FIG. 34, the absorbent core 24 can have three folding axes, first folding axis F1, second folding axis F2, and third folding axis F3. The second folding axis F2 and third folding axis F3 can be arranged relative to the first folding axis F1 such that the elastic member 200 lies adjacent portions of the first side 800 of absorbent core 24 between the second folding axis F2 and the third folding axis F3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine hygiene device comprising:
    an absorbent core comprising absorbent material and having a core longitudinal axis, said absorbent core having a first compressibility in an unaltered state, wherein at least a portion of said absorbent core that is generally aligned with said core longitudinal axis has a second compressibility in an altered state, wherein said second compressibility is greater than said first compressibility, wherein said portion of said absorbent core having said second compressibility is a part of said absorbent core from which absorbent material has not been completely removed; and
    an elastic member, said elastic member spanning at least a portion of said absorbent core having said second compressibility, said elastic member operatively related to said absorbent core, said elastic member generally aligned with said core longitudinal axis,
    wherein said feminine hygiene device has a middle area having a W-shaped cross section and a rear area having an inverted V-shaped cross section.

2. The feminine hygiene device of claim 1, wherein said portion of said absorbent core having said second compressibility is a preferentially weakened zone of compression.

3. The feminine hygiene device of claim 1, wherein said portion having said second compressibility comprises a slit intersecting said core longitudinal axis.

4. The feminine hygiene device of claim 1, wherein said portion having said second compressibility comprises intersecting slits, at least one of said slits intersecting said core longitudinal axis.

5. The feminine hygiene device of claim 4, wherein said intersecting slits are orthogonal to one another and one of said slits is generally orthogonal to said core longitudinal axis.

6. The feminine hygiene device of claim 1, wherein said portion having said second compressibility comprises corrugations crossing said core longitudinal axis.

7. The feminine hygiene device of claim 1, wherein said portion having said second compressibility comprises nodules.

8. The feminine hygiene device of claim 7, wherein a plurality of said nodules is disposed in said absorbent core in a diamond shaped region.

9. The feminine hygiene device of claim 1, wherein said portion having said second compressibility comprises tufts.

10. The feminine hygiene device of claim 1 further comprising a backsheet adjacent to said absorbent core, wherein said elastic member is between said absorbent core and said backsheet.

11. The feminine hygiene device of claim 1, wherein said elastic member is joined to said absorbent core.

12. The feminine hygiene device of claim 1 further comprising a backsheet adjacent to said absorbent core, wherein said elastic member is joined to said backsheet.

13. The feminine hygiene device of claim 1 further comprising a first folding axis generally orthogonal to said core longitudinal axis, wherein said feminine hygiene device is folded flat about said first folding axis to form an absorbent core first fold line.

14. The feminine hygiene device of claim 13, wherein a portion of said absorbent core first fold line is proximal a portion of said absorbent core having said second compressibility.

15. The feminine hygiene device of claim 13, wherein said elastic member is in tension when said feminine hygiene device is in an unfolded position and the tension in said elastic member when the feminine hygiene device is in a folded position is less than the tension in said elastic member when the feminine hygiene device is in an unfolded position.

16. The feminine hygiene device of claim 13, wherein said absorbent core first fold line is non-linear.

17. The feminine hygiene device of claim 13, wherein said elastic member is folded and said elastic member is folded at a different location than where said absorbent core is folded.

18. The feminine hygiene device of claim 13 further comprising a second folding axis generally orthogonal to said core longitudinal axis, wherein said feminine hygiene device is folded flat about said second folding axis to form an absorbent core second fold line.

19. The feminine hygiene device of claim 1 further comprising a topsheet and a backsheet, wherein said absorbent core is disposed between said topsheet and said backsheet, wherein said feminine hygiene device is a sanitary napkin.

20. A feminine hygiene device comprising:
an absorbent core comprising absorbent material and having a core longitudinal axis, said absorbent core having a first compressibility in an unaltered state, wherein at least a portion of said absorbent core that is generally aligned with said core longitudinal axis has a second compressibility comprising at least one preferentially weakened zone of compression, wherein said at least one preferentially weakened zone of compression has a zone width extending in a direction that is generally orthogonal to said core longitudinal axis and measuring from about 10 mm up to the entire width of said absorbent core; and
an elastic member, said elastic member spanning at least a portion of said absorbent core having said second compressibility, said elastic member operatively related to said absorbent core, said elastic member generally aligned with said core longitudinal axis.

* * * * *